(12) United States Patent
Joye et al.

(10) Patent No.: US 7,862,557 B2
(45) Date of Patent: Jan. 4, 2011

(54) CRYOTHERAPY METHODS FOR TREATING VESSEL DISSECTIONS AND SIDE BRANCH OCCLUSION

(75) Inventors: James Joye, Monte Sereno, CA (US); Kristine Tatsutani, Oakland, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1285 days.

(21) Appl. No.: 10/867,986

(22) Filed: Jun. 14, 2004

(65) Prior Publication Data

US 2004/0243116 A1 Dec. 2, 2004

Related U.S. Application Data

(63) Continuation of application No. 09/953,500, filed on Sep. 14, 2001, now Pat. No. 6,786,900.

(60) Provisional application No. 60/312,295, filed on Aug. 13, 2001.

(51) Int. Cl.
*A61B 18/02* (2006.01)
(52) U.S. Cl. .......................... 606/21; 606/23
(58) Field of Classification Search ............. 606/20–26, 606/41
See application file for complete search history.

(56) References Cited

U.S. PATENT DOCUMENTS

| | | | |
|---|---|---|---|
| 3,901,241 A | 8/1975 | Allen, Jr. | |
| 4,336,691 A | 6/1982 | Burnstein et al. | |
| 4,754,752 A | 7/1988 | Ginsburg et al. | |
| 5,019,075 A | 5/1991 | Spears et al. | |
| 5,041,089 A | 8/1991 | Mueller et al. | |
| 5,078,713 A | 1/1992 | Vaney | |
| 5,092,841 A | 3/1992 | Spears | |
| 5,106,360 A | 4/1992 | Ishiwara et al. | |
| 5,147,355 A | 9/1992 | Friedman et al. | |

(Continued)

FOREIGN PATENT DOCUMENTS

WO    WO 91/05528 A1    5/1991

(Continued)

OTHER PUBLICATIONS

Case of the Dav: IVUS Still Images—Case 19, found at http://ccal.stanford.edu/case/casel 9/stills.html.

(Continued)

*Primary Examiner*—Michael Peffley
(74) *Attorney, Agent, or Firm*—Vidas, Arrett & Steinkraus

(57) ABSTRACT

The present invention provides cryotherapy treatment of dissections in a blood vessel of a patient. The present invention further provides cryotherapy treatment of side branch occlusion in a bifurcated blood vessel. One method for treating potential or existing dissections in a blood vessel comprises cooling the blood vessel to a temperature and for a time sufficient to remodel the blood vessel such that dissections of the blood vessel are reduced. Another method for treating side branch occlusion in a bifurcated blood vessel, the bifurcated blood vessel having a side branch and a main branch, the main branch having plaque disposed thereon, comprises cooling an inner surface of the main branch to a temperature and for a time sufficient to inhibit plaque shift from the main branch into the side branch.

13 Claims, 18 Drawing Sheets

U.S. PATENT DOCUMENTS

| | | |
|---|---|---|
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,275,595 A | 1/1994 | Dobak, III |
| 5,411,466 A | 5/1995 | Hess |
| 5,458,612 A | 10/1995 | Chin |
| 5,486,208 A | 1/1996 | Ginsberg |
| 5,501,681 A | 3/1996 | Neuwirth et al. |
| 5,545,195 A | 8/1996 | Lennox et al. |
| 5,617,739 A | 4/1997 | Little |
| 5,644,502 A | 7/1997 | Little |
| 5,733,280 A | 3/1998 | Avitall |
| 5,868,735 A | 2/1999 | Lafontaine |
| 5,902,299 A | 5/1999 | Jayaraman |
| 5,971,979 A | 10/1999 | Joye et al. |
| 6,241,718 B1 | 6/2001 | Arless et al. |
| 6,290,696 B1* | 9/2001 | Lafontaine .................. 606/21 |
| 6,355,029 B1 | 3/2002 | Joye et al. |
| 6,709,440 B2* | 3/2004 | Callol et al. ............... 606/108 |
| 6,786,900 B2* | 9/2004 | Joye et al. .................... 606/21 |
| 6,875,209 B2* | 4/2005 | Zvuloni et al. ............... 606/21 |

FOREIGN PATENT DOCUMENTS

| | | |
|---|---|---|
| WO | WO 98/38934 A1 | 11/1998 |
| WO | WO 01/64145 A1 | 11/2001 |
| WO | WO 02/04042 A2 | 1/2002 |
| WO | WO 02/07625 A2 | 1/2002 |

OTHER PUBLICATIONS

Case of the Day: IVUS Still Images—Case 29, Adapted from Geber et al. Am. J. Cardiol., 1992; 70; pp. 1546-1554. found at http://ccal.stanford.edu/case/case29/stills.html.

Chevalier et al., "Placement of coronary stents in bifurcation lesions by the 'Culotte' technique," Am. J. Cardiol (1998) 82:943-949.

Lefevre et al., "Stenting of bifurcation lesions: Classification, treatments, and results," Cathet. Cardiovasc. Intervent (2000) 49:274-283.

Oesterle, "Angioplasty techniques for stenoses involving coronary artery bifurcations," Am. J. Cardiol. (1988) 61:29G-32G.

Web Page entitled "Cutting Balloon: A new generation of dilatation," printed from http://www.Interventionaltech.com/Products/CuttingBalloon.html on Oct. 24, 2001, 1 page total.

Zorger et al., "Clinical Studies: Peripheral Arterial Balloon Angioplasty: Effect of Short versus Long Balloon Inflation Times on the Morphologic Results," JVIR, vol. 13, No. 4, Apr. 2002, pp. 355-359.

* cited by examiner

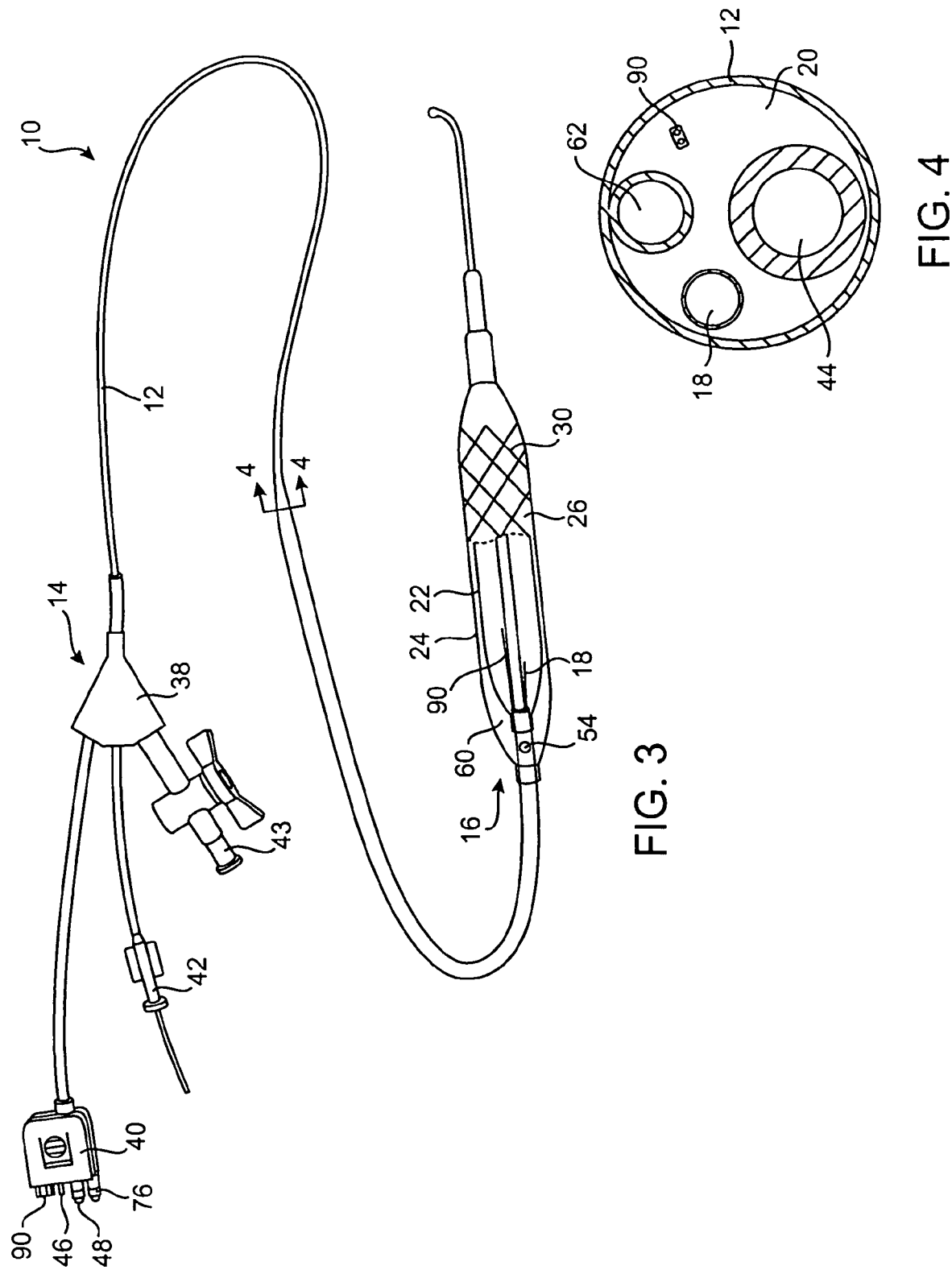

Diffuse, Adductor Canal Lesion

Focal, Popliteal Artery Stenosis

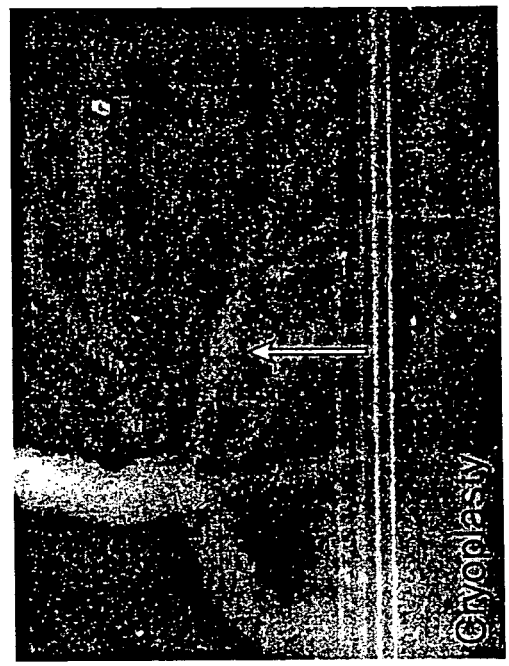
FIG. 13B
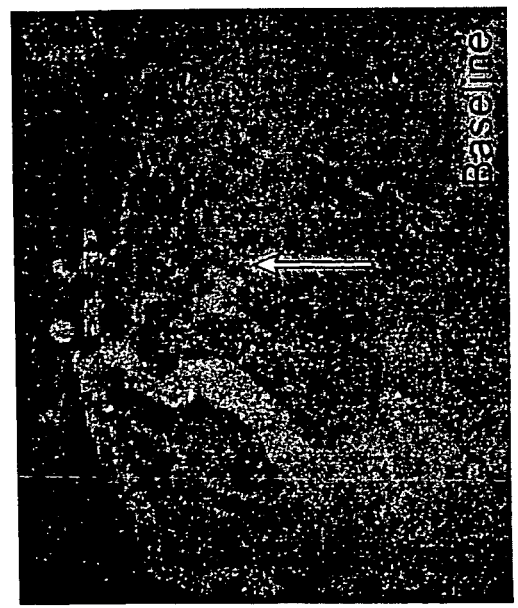
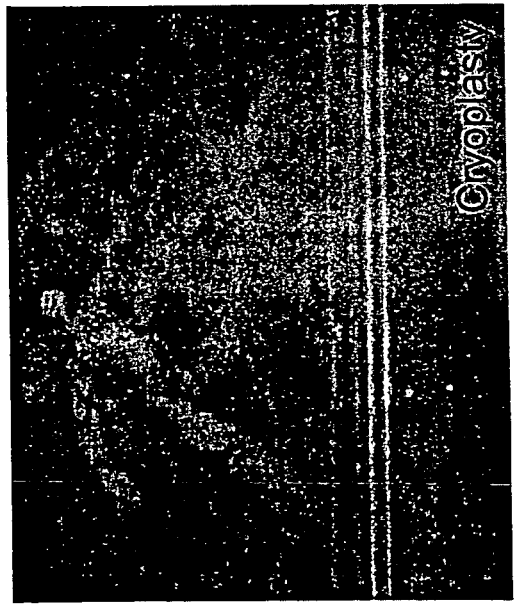
FIG. 13A

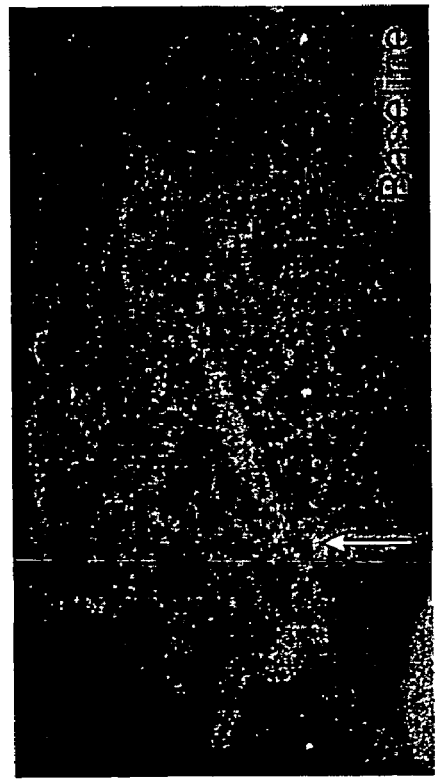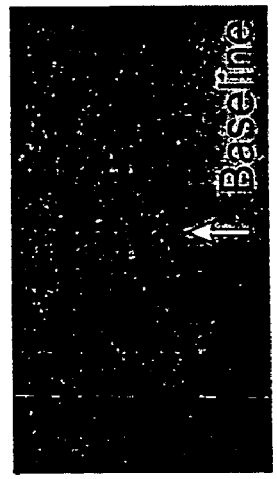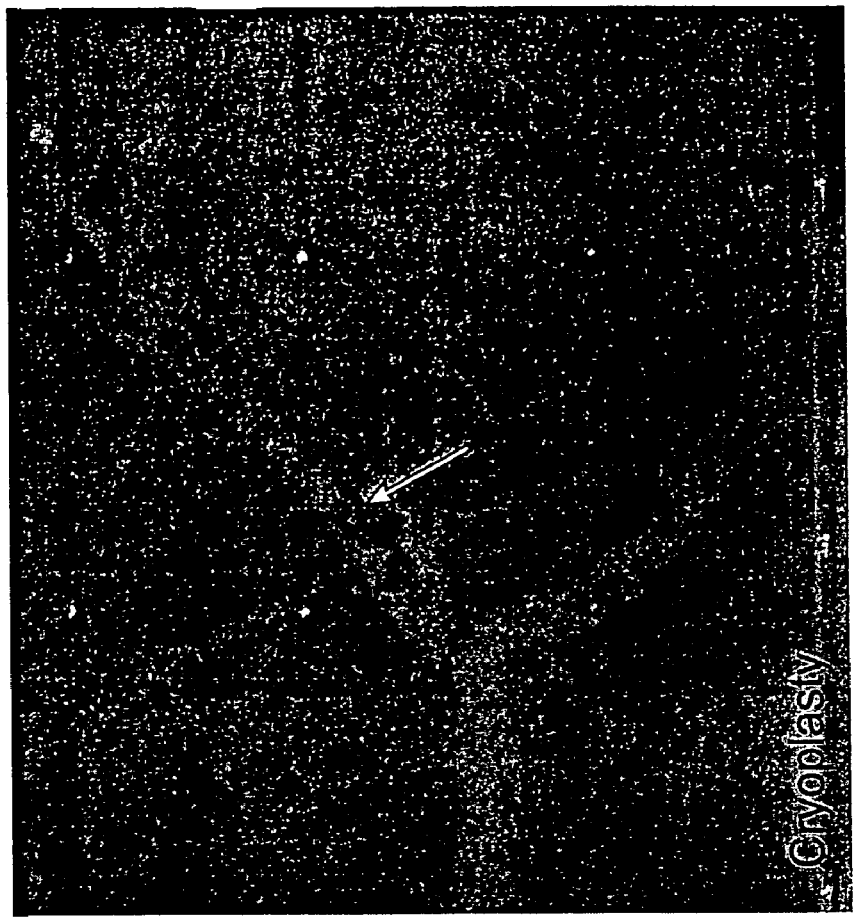
FIG. 13C
Subtotal LAD Occlusion

Calcified Circumflex Lesion

RCA In-Stent & De Novo Disease

CRYOTHERAPY METHODS FOR TREATING VESSEL DISSECTIONS AND SIDE BRANCH OCCLUSION

CROSS-REFERENCE TO RELATED APPLICATION

This is a continuation of U.S. patent application No. 09/953,500 filed on Sep. 14, 2001, now issued U.S. Pat. No. 6,786,900, which claims the benefit under 35 U.S.C. §119(e) of U.S. Provisional Application No. 60/312,295 filed on Aug. 13, 2001, the full disclosures of which are incorporated herein by reference.

BACKGROUND OF THE INVENTION

1. Field of the Invention

The present invention relates generally to medical methods and kits. More particularly, the present invention provides methods and kits for cryogenically cooling a blood vessel within a patient's vasculature to treat potential or existing dissections in the blood vessel. The present invention further provides methods and kits for cryogenically cooling a bifurcated blood vessel to treat side branch occlusion. Vessel dissections and side branch occlusion often result from angioplasty or other intravascular procedures for treating atherosclerosis and other diseases of the vasculature.

Atherosclerotic plaque is present to some degree in most adults. Plaques can severely limit the blood flow through a blood vessel by narrowing the open vessel lumen. This narrowing effect or stenosis is often responsible for ischemic heart disease. Fortunately, a number of percutaneous intravascular procedures have been developed for treating atherosclerotic disease in a patient's vasculature. The most successful of these treatments is percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these percutaneous intravascular procedures, particularly PTA, have provided significant benefits for treatment of stenosis caused by plaque, they continue to suffer from significant disadvantages. Particularly common disadvantages are the subsequent occurrence of vessel dissection, vessel recoil (acute and delayed), side branch occlusion, restenosis, and other procedure related trauma. Such disadvantages may affect up to 80% of all angioplasty patients to some extent.

During conventional PTA, the inflated balloon tends to create large fissures or tears in the intima of the blood vessel wall, particularly at a junction between the plaque and the vessel wall. Such tears or fissures are referred to as dissections. Vessel dissections compromise the dilated vessel, often constricting or blocking blood flow within the vessel. A number of strategies have been proposed to treat vessel dissections. Previously proposed strategies include prolonged balloon inflation, treatment of the blood vessel with a heated balloon, stenting of the region following balloon angioplasty, and the like. While these proposal have enjoyed varying levels of success, no one of these procedures is proven to be entirely successful. In particular, stenting of the dilated region may address acute problems of intimal dissection and vessel recoil, however stents are believed to actually cause a marked increase in the degree of intimal restenosis or hyperplasia (re-narrowing of the an artery following an initially successful angioplasty). This in turn leads to greater late luminal loss, especially in smaller vessels which are more susceptible to re-closure due to restenosis. Moreover, stents may prove to be an impractical solution when dilating long periphery arteries that may require multiple stent placements. Stents may additionally not always be easily maneuvered to and positioned in dilated regions, especially in the coronary arteries.

Another limitation associated with angioplasty is side branch occlusion in a bifurcated blood vessel during dilatation of a primary vessel lesion. Side branch occlusion can occur by several mechanisms. The "snow plow" effect may be the most common mode of side branch occlusion, in which plaque from a primary vessel is literally "plowed" or "shifted" into the adjacent side vessel during dilatation, narrowing or occluding the side vessel lumen. Known procedures for treating side branch occlusion include the "kissing balloon technique" where two guiding catheters are positioned in the bifurcated vessel, one in the primary vessel and the other in the side branch, and the balloons are inflated simultaneously or sequentially so that they potentially touch or "kiss." However, such angioplasty techniques alone or in combination with stents, has not been entirely successful in preventing side branch occlusion.

For these reasons, it would be desirable to provide methods and kits for the treatment of dissections in a blood vessel. It would be further desirable to provide methods and kits for the treatment of side branch occlusion in a bifurcated blood vessel. The methods should be suitable for intravascular and intraluminal introduction, preferably via a percutaneous approach. It would be particularly desirable if the new methods were able to deliver the treatment in a very controlled and safe manner with minimum side effects. At least some of these objectives will be met by the invention described herein.

2. Description of the Background Art

Cryoplasty methods and devices are described in co-pending U.S. patent application Ser. No. 08/982,824, now U.S. Pat. No. 5,971,979; U.S. patent application No. 09/203,011 , now issued U.S. Pat. No. 6,355,029; U.S. patent application Ser. No. 09/510,903, now issued U.S. Pat. No. 6,428,534; U.S. patent application Ser. No. 09/619,583, now issued U.S. Pat. No. 6,514,245, assigned to the assignee of the present application. A cryoplasty device and method are also described in WO 98/38934. Balloon catheters for intravascular cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901, 241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336, 691. The following U.S. Patents may also be relevant to the present invention: 5,458,612; 5,545,195; and 5,733,280.

Side branch occlusion is described by Stephen N. Oesterle in *Angioplasty Techniques for Stenoses Involving Coronary Artery Bifurcations*, Am J Cardiol, vol. 61, pp. 29G-32G (1988); Lefevre et al. in *Stenting of Bifurcation Lesions: Classification, Treatments, and Results*, Catheterization and Cardiovascular Interventions, vol. 49, pp. 274-283 (2000); Chevalier et al. in *Placement of Coronary Stent in Bifurcation Lesions by the "Culotte" Technique*, Am J Cardiol, vol. 82, pp. 943G-949G (1998). Cutting balloons are described at http://www.interventionaltech.com/Products/CuttingBallon.html. The full disclosures of each of the above references are incorporated herein by reference.

BRIEF SUMMARY OF THE INVENTION

The present invention provides cryotherapy treatment of dissections in a blood vessel of a patient. The present invention further provides cryotherapy treatment of side branch occlusion in a bifurcated blood vessel. The blood vessel may be any blood vessel in the patient's vasculature, including veins, arteries, and particularly coronary arteries. The blood vessel will be at least partially stenosed, typically by eccentric calcified plaque (i.e. the plaque compromises a vessel lumen predominantly from one side) in the coronary and peripheral arteries. In particular, the present invention may limit, reduce, minimize, prevent, mitigate, and/or inhibit potential or existing dissections of a vessel and/or plaque shift from a main branch into a side branch of a bifurcated blood vessel so as to inhibit acute coronary syndrome.

In a first aspect, the present invention provides a method for treating potential or existing dissections in a blood vessel. The method comprises cooling the blood vessel to a temperature and for a time sufficient to remodel the blood vessel such that dissections of the blood vessel are reduced. The cooling treatment will often be directed against all or a portion of a circumferential surface of a lumen of the blood vessel.

Cooling of a vessel may be effected by introducing a catheter into a lumen of a blood vessel. A balloon is positioned within the vessel lumen adjacent the potential or existing dissection. Cryogenic cooling fluid is introduced into the balloon and exhausted. The balloon expands to radially engage the vessel lumen. Generally, the cooling temperature at the cell surface of the blood vessel lumen is in a range from about −3° C. to about −15° C. The tissue is typically maintained at the desired temperature for a time period in the range from about 10 seconds to about 60 seconds, more preferably from about 20 seconds to about 40 seconds. Vessel dissection treatment may be enhanced by repeating cooling in cycles, typically with from about 1 cycle to 3 cycles, with the cycles being repeated at a rate of about one cycle every 60 seconds.

The dissections may comprise flaps, residual plaque, and/or pieces of tissue resulting from fissuring or tearing of the intima of the blood vessel wall or plaque thereon. Typically, such dissections occur at a junction between the plaque and the vessel wall, wherein the plaque tears at its margins and sends a plane of dissection deep into the media of the vessel wall. Dissections are undesirable as they often compromise the integrity of the blood vessel by at least partially blocking the blood vessel. Such blockage can limit blood flow and potentially create a threat to acute vessel closure. The dissections may further create flow in an abnormal pattern (i.e. flow in planes other than the true vessel lumen or non laminar flow.)

The blood vessel is subject to dissections resulting from treatment of a stenosis, wherein the treatment of the stenosis typically comprises percutaneous transluminal angioplasty. The cooling step may be performed before or after balloon angioplasty, and will preferably be performed during balloon angioplasty. Surprisingly, work in connection with the present invention has shown that cooling of the blood vessel reduces and/or inhibits potential or existing dissections so as to produce a "stent-like" angiographic result (i.e. dissection free lumen without the use of a stent). Moreover, cooling may further minimize or inhibit restenosis or hyperplasia (re-narrowing of the an artery following an initially successfull angioplasty) and help maintain the patency of a body lumen. Cooling may also be efficiently effected in long periphery arteries and the cooling apparatus easily maneuvered to and positioned in the treatment vessel, especially in the coronary arteries, so that cooling may be effected in difficult to access areas.

The cooling step may alter mechanical properties of the blood vessel wall or plaque thereon so the that fissuring or tearing of the blood vessel wall or plaque thereon is reduced. Particularly, the blood vessel wall and/or plaque is solidified so that there is not such a great disparity in compliance between the two. As such, the dilatation force applied by the angioplasty cooling balloon is more evenly distributed around a circumference of the vessel wall so that tearing of the vessel at the junction between the vessel wall and plaque is minimized (i.e. any resulting fissures in the vessel wall and plaque are small or micro cracks that do not compromise flow in the vessel). Cooling may also alter a fail mode of the vessel resulting from the modified mechanical properties. Cooling may alternatively or additionally enhance bonding between layers of the blood vessel wall so that fissuring or tearing of the blood vessel wall is reduced. In other applications, the cooling step may tack or re-attach existing vessel dissections, resulting from a prior angioplasty procedure, into the blood vessel wall.

In some instances, cooling may soften or weaken the vessel wall or plaque thereon, particularly eccentric calcified plaque, so that the vessel can be dilated or expanded at much lower pressures than is used with conventional angioplasty. Specifically, cooling temperatures of about −10° C. may freeze fluid between spaces in the calcium which in turn breaks up the calcified plaque, softening the vessel so that it can dilated at a lower pressure. In addition to the softening or weakening of the vessel wall or plaque thereon, cooling at low temperatures may also freeze and harden non-treatment tissue adjacent to the calcified plaque so that the vessel wall may exhibit more uniform properties against the dilation force applied by the angioplasty cooling balloon.

In another aspect, the present invention provides a method for treating potential or existing dissections in a blood vessel, said method comprising introducing a catheter into a lumen of the blood vessel and positioning a balloon within the vessel lumen adjacent the potential or existing dissection. Cryogenic cooling fluid is introduced into the balloon and exhausted. The balloon is expanded to radially engage the vessel lumen and cool the vessel lumen to a temperature and for a time sufficient to remodel the blood vessel such that dissections of the blood vessel are reduced and/or inhibited. Cooling may comprise adhering the cooling balloon to the blood vessel or plaque thereon so as to minimize any slippage of the cooling balloon. This is particularly advantageous in the treatment of a stenosis as plaque is often amorphous and slippery and as such conventional uncooled angioplasty balloons often slip and cause additional dissections or tears proximal and distal of the stenosis. Hence, cooling prevents the creation of any additional dissections by minimizing such slippage of the cooling balloon and in so doing further allows for controlled dilatation at the stenosis.

In another aspect, the present invention provides a method for treating side branch occlusion in a bifurcated blood vessel, the bifurcated blood vessel having a side branch and a main branch, the main branch having plaque disposed thereon. In some instances, the side branch may also be at least partially stenosed. The method comprises introducing a catheter into a lumen of the main branch and positioning a balloon within the main branch adjacent the plaque. Cryogenic cooling fluid is introduced into the balloon and exhausted. The balloon is expanded to radially engage the main branch lumen and an inner surface of the main branch is cooled to a temperature and for a time sufficient to inhibit plaque shift from the main or primary branch into the adjacent or side branch.

The plaque comprises a combination of calcified, fatty, and fibrous tissues and is fairly amorphous and slippery so that it easily shifts by its structural nature. As such, the side branch is often subject to occlusion by plaque shift from the main branch into the side branch as a result of treatment of plaque in the main branch. Treatment of the plaque typically comprises balloon angioplasty, wherein the cooling step may be performed before, after, or preferably during balloon angioplasty. In some instances, the treatment of plaque in the main branch may be accompanied by simultaneous or sequential treatment of stenosis in the side branch. It is believed that the cooling step alters mechanical properties of the plaque (i.e. plaque compliance) so that plaque shift from the main branch to the side branch is inhibited. In particular, cooling may solidify the plaque so that it less amorphous and thus less susceptible to shifting. Plaque solidification may further be enhanced by the formation of a temporary ice cap on an orifice of the side branch due to a small portion of the cryoplasty balloon coming into contact with blood cells.

In yet another aspect, the present invention provides a kit for treating potential or existing dissections in a blood vessel. The kit comprises a catheter having a proximal end, a distal end, and a cooling member. Instructions are included in the kit for use of the catheter. These instructions may comprise the step of cooling the blood vessel adjacent the potential or existing dissection to remodel the blood vessel such that dissections of the blood vessel are reduced. The kit may additionally or alternatively provide for the treatment of side branch occlusion in a bifurcate vessel, wherein the instructions recite the step of cooling a main branch lumen adjacent the plaque to inhibit plaque shift from the main branch into the side branch. Such kits may include instructions for performing one or more of the above described methods. The instructions will often be printed, optionally being at least in-part disposed on packaging. The instructions may alternatively comprise a videotape, a CD-ROM or other machine readable code, a graphical representation, or the like showing any of the above described methods.

In another aspect, the present invention provides a method for treating potential elastic recoil in a blood vessel, the method comprising introducing a catheter into a lumen of the blood vessel and positioning a balloon within the vessel lumen adjacent tissue that may potentially recoil. The balloon is expanded to radially engage the vessel lumen and cool the vessel lumen to a temperature and for a time sufficient to remodel the blood vessel such that actual elastic recoil is inhibited.

The cooling step may alter structural properties of collagen fibers of the vessel wall such that elastic recoil of the vessel is reduced. In particular, induction of a phase change in an aqueous component of the adjacent tissue during cooling may cause acute structural changes to the tissue matrix. Dilatation of the vessel by the cooling balloon may be accompanied by a drop in a balloon surface temperature below a phase transition threshold of physiologic saline. Thus, as the balloon expands and experiences a temperature drop, the aqueous saline in interstitial spaces (i.e. spaces between cells and fibers that constitute the vessel wall) in the adjacent tissue begin to freeze. As such, ice may be nucleated in the interstitial spaces and propagate radially outward through the tissue. The expanding ice may in turn impose mechanical compressive forces on collagen fibers and vessel cells. Correspondingly, the collagen fibers and cells may undergo morphological deformation in response to the mechanical forces. Any plastic deformation of the collagen fibers may produce permanent or semi-permanent alteration of the vessel tissue, and consequently may yield an alternation in the structural properties of the tissue. Specifically, possible compacting or compression of collagen fibers by cooling may substantially alter structural properties, such as elasticity, of the collagen fibers so that elastic recoil of the vessel is reduced.

The blood vessel is typically subject to elastic recoil resulting from treatment of a stenosis. The treatment of stenosis typically comprises balloon angioplasty, wherein the cooling step may be performed before, after, or preferably during balloon angioplasty. Moreover, during balloon angioplasty the vessel is being expanded by balloon expansion which may exert radially directed mechanical forces on the vessel tissue. Hence, the dual action of mechanical compressive forces generated by concurrent dilation and cooling may produce a more beneficial effect than can be achieved by conventional angioplasty.

In a still further aspect, the present invention provides a method for producing a smooth luminal surface in a blood vessel that is at least partially stenosed by fatty plaque, said method comprising introducing a catheter in a lumen of the blood vessel and positioning a balloon within the vessel lumen adjacent the fatty plaque. The balloon is expanded to radially engage the vessel lumen and cool the vessel lumen to a temperature and for a time sufficient to remodel the blood vessel so as to produce a smooth luminal surface. In particular, fatty lipid based plaque may undergo chemical or physical alterations in response to cooling of the plaque below a lipid phase change temperature (typically being in a range from about +15° C. to about 0° C.). This remodeling of the vessel and plaque thereon may in turn produce a smoother luminal surface than can be achieved with conventional angioplasty. A smoother luminal surface advantageously provides more laminar flow through the vessel wall, and further reduces any shear stresses on the vessel wall.

BRIEF DESCRIPTION OF THE DRAWINGS

FIG. 3 illustrates a cryotherapy catheter for treating vessel dissections and side branch occlusion constructed in accordance with the principles of the present invention.

FIG. 4 is a cross-sectional view of the catheter taken along line 4-4 in FIG. 3.

DETAILED DESCRIPTION OF THE INVENTION

Figure 1A:
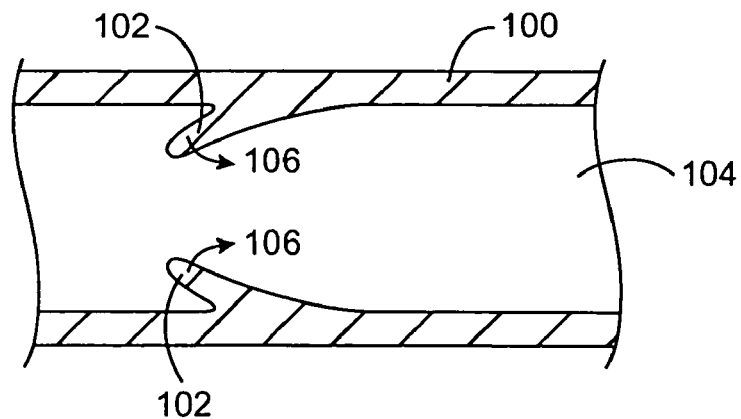
FIGS. 1A-1C are cross-sectional views of blood vessels having dissections.
Figure 1B:
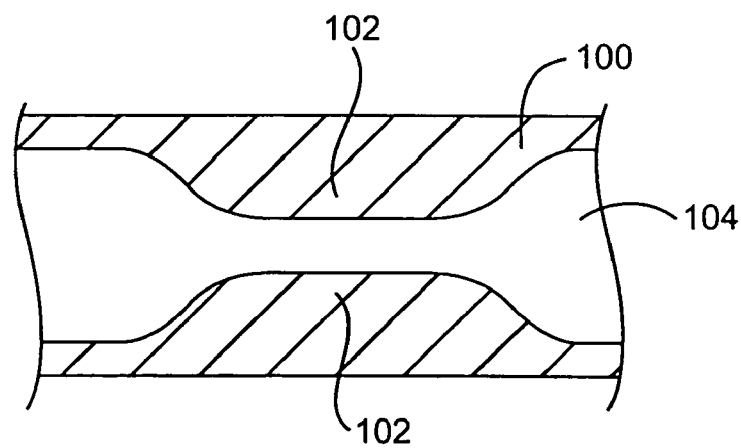
Figure 1C:
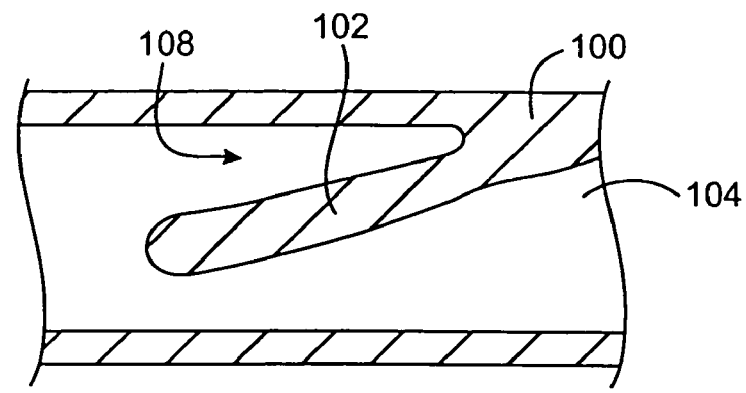

The present invention provides cryotherapy treatment of dissections in a blood vessel of a patient. FIGS. 1A-1C illustrate cross-sectional views of a blood vessel 100 having dissections 102 within a lumen 104 of the vessel. The dissections 102 generally comprise flaps, residual plaque, and/or pieces of tissue resulting from fissuring or tearing of the intima of the blood vessel wall or plaque thereon from primary treatments like balloon angioplasty. Typically, such dissections 102 occur at a junction between the plaque and the vessel wall, wherein the plaque tears at its margins and sends a plane of dissection deep into the media of the vessel wall. As shown in FIG. 1B, dissections 102 are undesirable as they often compromise the integrity of the blood vessel by at least partially blocking the blood vessel 100. For example, the dissection 102 may shift in direction 106 to limit blood flow and potentially create a threat to acute vessel closure (FIG. 1B). Dissections 102 may further create flow in planes other than the true vessel lumen as depicted by arrow 108.

Figure 2A:
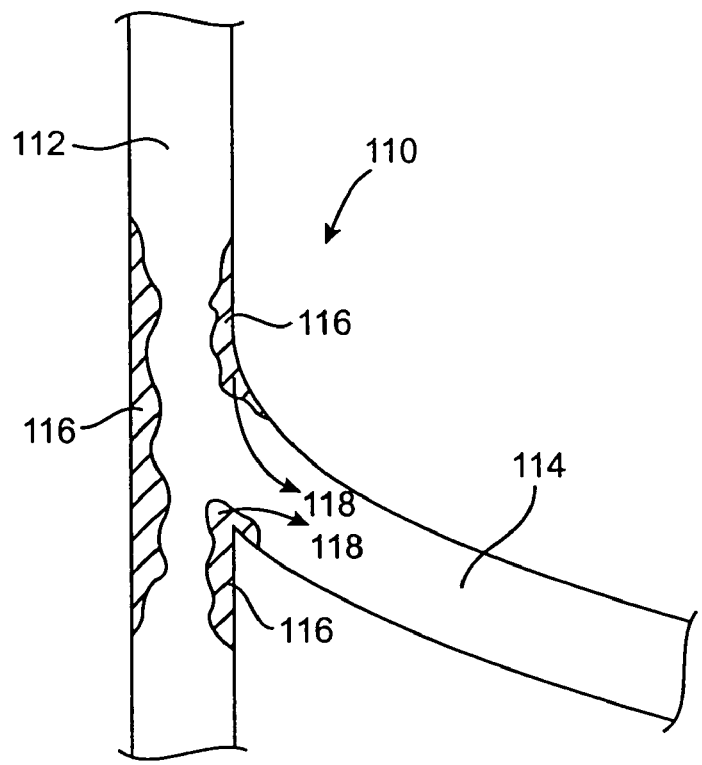
FIG. 2A is a cross-sectional view of a stenosed bifurcated blood vessel.
Figure 2B:
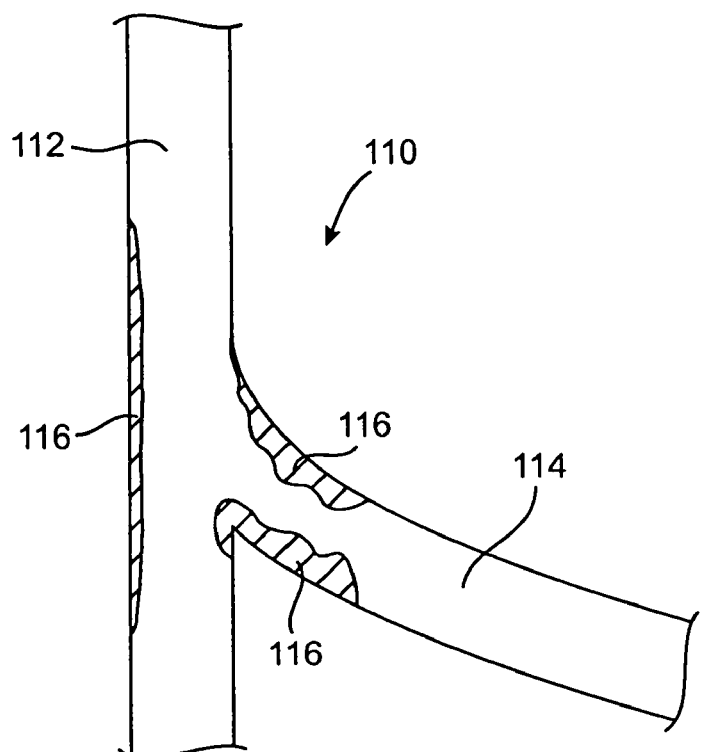
FIG. 2B is a cross-sectional view illustrating plaque shift in the bifurcated blood vessel.

The present invention further provides cryotherapy treatment of side branch occlusion in a bifurcated vessel. FIG. 2A illustrates a bifurcated blood vessel having a main or primary branch 112 and an adjacent or side branch 114. The main branch 112 is at least partially stenosed 116. The plaque 116 generally comprises a combination of calcium, fat, and lipids and is fairly amorphous and slippery so that it easily shifts by its structural nature. As such, the side branch 114 is often subject to occlusion by plaque shift from the main branch 112 into the side branch 114, as depicted by arrows 118, as a result of treatment of plaque in the main branch. Treatment of plaque typically comprises balloon angioplasty, wherein balloon dilatation shifts the plaque 116 into the side branch 114 as shown in FIG. 2B, narrowing or occluding the side branch lumen and potentially creating a threat to acute vessel closure.

Referring now to FIGS. 3 and 4, a cryotherapy catheter 10 (which is more fully described in co-pending application Ser. No. 09/619,583 filed Jul. 19, 2000, the full disclosure of which is incorporated herein by reference) for treating dissections 102 in a blood vessel 100 (see FIG. 1A) and/or side branch occlusion (see FIG. 2B) will be described. The catheter 10 comprises a catheter body 12 having a proximal end 14 and a distal end 16 with a cooling fluid supply lumen 18 and an exhaust lumen 20 extending therebetween. A first balloon 22 is disposed near the distal end of the catheter body 12 in fluid communication with the supply and exhaust lumens. A second balloon 24 is disposed over the first balloon 22 with a thermal barrier 26 therebetween. It will be appreciated that the following depictions are for illustration purposes only and does not necessarily reflect the actual shape, size, or dimensions of the cryotherapy catheter 10. This applies to all depictions hereinafter.

The balloons 22, 24 may be an integral extension of the catheter body 12, but such a structure is not required by the present invention. The balloons 22, 24 could be formed from the same or a different material as the catheter body 12 and, in the latter case, attached to the distal end 16 of the catheter body 12 by suitable adhesives, heat welding, or the like. The catheter body 12 may be formed from conventional materials, such as polyethylenes, polyimides, and copolymers and derivatives thereof. The balloons 22, 24 may also be formed from conventional materials used for angioplasty, preferably being inelastic, such as nylon, polyethylene terephthalate (PET), or polyethylene, elastic, such as urethane, latex, or silicone, or other medical grade material suitable for constructing a strong non-distensible balloon. Additionally, balloons 22 and 24 could be formed from different material to provide improved protection. For example, the first balloon 22 could be formed from PET to provide strength while the second balloon 24 could be formed from polyethylene to provide durability. The balloons 22, 24 have a length of at least 1 cm each, more preferably in the range from 2 cm to 5 cm each in a coronary artery and 2 cm to 10 cm each in a periphery artery. The balloons 22, 24 will have diameters in the range from 2 mm to 5 mm each in a coronary artery and 2 mm to 10 mm each in a peripheral artery.

The thermal barrier 26 may comprise a gap maintained between the balloons 22, 24 by a filament. The filament typically comprises a helically wound, braided, woven, or knotted monofilament. The monofilament may be formed from PET or polyethylene napthlate (PEN), and affixed to the first balloon 22 by adhesion bonding, heat welding, fasteners, or the like. The thermal barrier 26 may also comprise a gap maintained between the balloons 22, 24 by a plurality of bumps on an outer surface of the first balloon 22 and/or an inner surface of the second balloon 24. The plurality of bumps may be formed in a variety of ways. For example, the bumps may be intrinsic to the balloon (created during balloon blowing), or the bumps could be created by deforming the material of the balloon wall, by affixing mechanical "dots" to the balloon using adhesion bonding, heat welding, fasteners, or the like. Alternatively, the thermal barrier 26 may comprise a gap maintained between the balloons 22, 24 by a sleeve. The sleeve may be perforated and formed from PET or rubbers such as silicone and polyurethane.

Hubs 34 and 36 are secured to the proximal end 14 of the catheter body 12. Hub 34 provides a port 38 for connecting a cryogenic fluid source to the fluid supply lumen 18 which in turn is in fluid communication with the inner surface of the first balloon 22. Hub 34 further provides a port 40 for exhausting the cryogenic fluid which travels from balloon 22 in a proximal direction through the exhaust lumen 20. Hub 36 provides a port 42 for a guidewire which extends through a guidewire lumen 44 in the catheter body 12. Typically, the guidewire lumen 44 will extend through the exhaust lumen 20, as shown in FIG. 4. The guidewire lumen 44 may also extend axially outside the exhaust lumen 20 to minimize the occurrence of cryogenic fluid entering the blood stream via the guidewire lumen 44. Optionally, the guidewire lumen 44 may extend outside the inner surface of the first balloon 22 or the guidewire lumen 44 may allow for a guidewire to extend outside both balloons 22, 24. Additionally, a reinforcing coil 46 may extend along the catheter body 12 proximal the first balloon 22. The reinforcing coil 46 may comprise a simple spring having a length typically in the range from 6 cm to 10 cm to prevent the catheter 10 from kinking up inside the blood vessel.

The cryotherapy catheter 10 in FIG. 3 additionally illustrates a safety mechanism that monitors the containment of the first and second balloons 22, 24. The first balloon 22 defines a volume in fluid communication with the supply and exhaust lumens. A fluid shutoff is coupled to a cryogenic fluid supply with the supply lumen 18. The second balloon 24 is disposed over the first balloon 22 with a vacuum space 52 therebetween. The vacuum space 52 is coupled to the fluid shutoff so as to inhibit flow of cryogenic fluid into the first balloon 22 in response to a change in the vacuum space 52.

Figure 5:
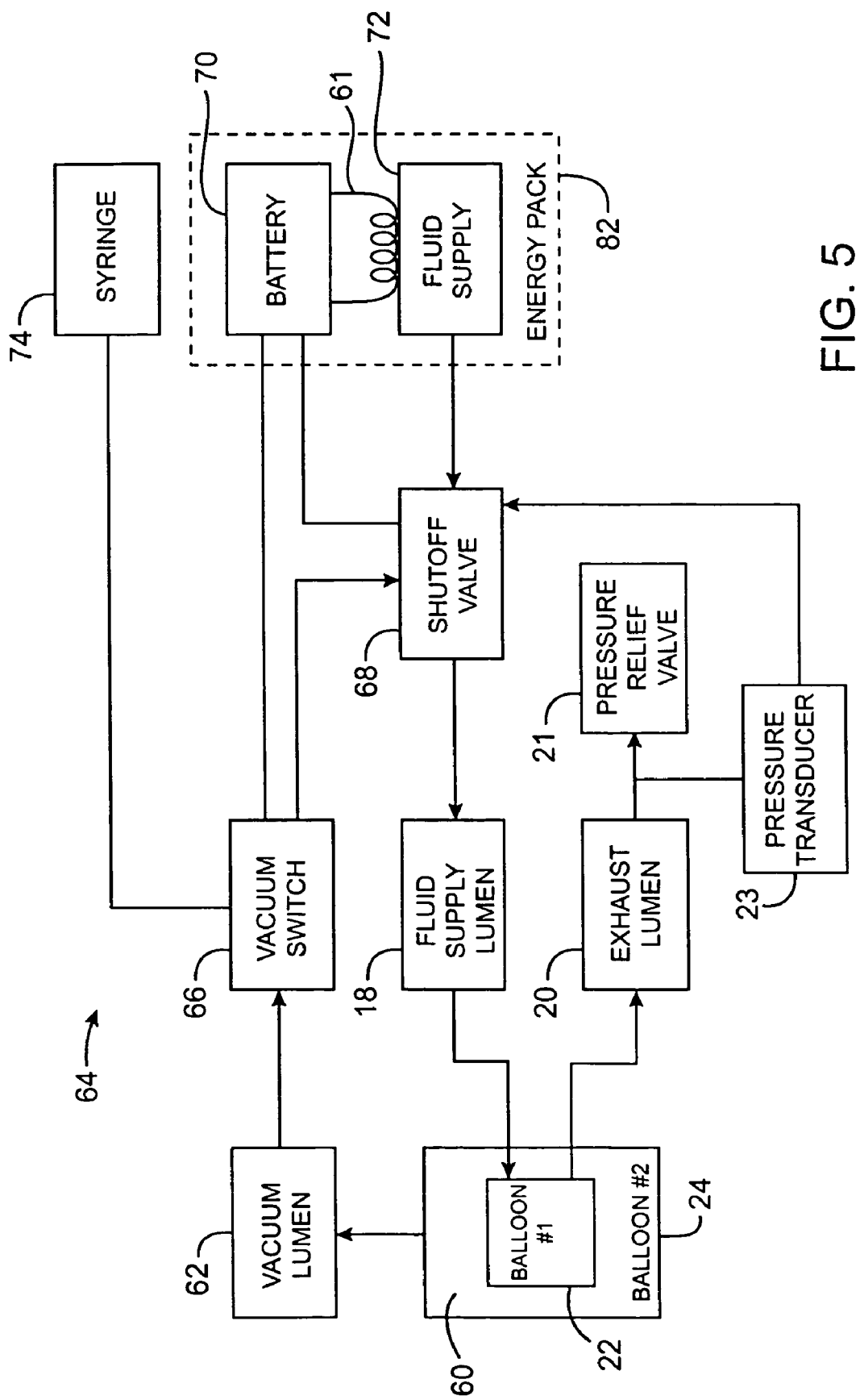
FIG. 5 is a functional flow diagram illustrating the operation of automatic fluid shutoff mechanism of the catheter of FIG. 3.

FIG. 5 illustrates a functional flow diagram of the automatic fluid shutoff mechanism 54. The fluid shutoff 54 typically comprises a vacuum switch 56 connected to a shutoff valve 58 by a circuit, the circuit being powered by a battery 60. The switch 56 may remain closed only when a predetermined level of vacuum space 52 is detected in the second balloon 24. The closed switch 56 allows the shutoff valve 58, in fluid communication with the cryogenic fluid supply 62, to be open. Alternatively, the circuit may be arranged so that the switch 56 is open only when the predetermined vacuum space 52 is present, with the shutoff valve 58 being open when the switch is open. The vacuum space 52 is reduced when either the first balloon 22 is punctured, allowing cryogenic fluid to enter the vacuum space 52, or the second balloon 24 is punctured, allowing blood to enter the vacuum space 52. In addition to monitoring the containment of both balloons 22, 24, in the event of a failure, the vacuum switch 56 will be triggered to prevent the delivery of additional cryogenic fluid from the fluid supply 62 into the supply lumen 18. The second balloon 24 also acts to contain any cryogenic fluid that may have escaped the first balloon 22. The exhaust lumen 20 is fluidly connected to a pressure relief valve 21 which in turn will typically vent to atmosphere. In some instances, a pressure transducer 23 will also trigger the shutoff valve 58 when a particular threshold pressure is measured.

Figure 6:
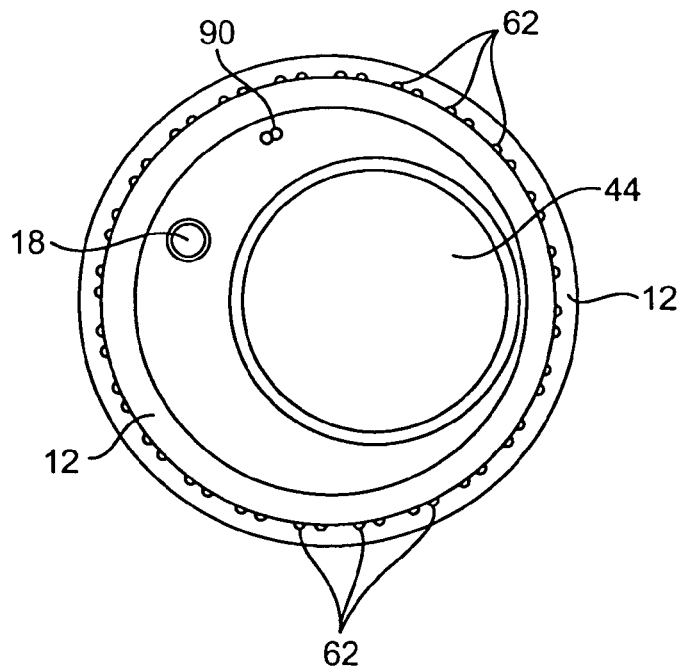
FIGS. 6 and 7 illustrate a handle and removable energy pack for use in the cryotherapy catheter of FIG. 3.
Figure 7:
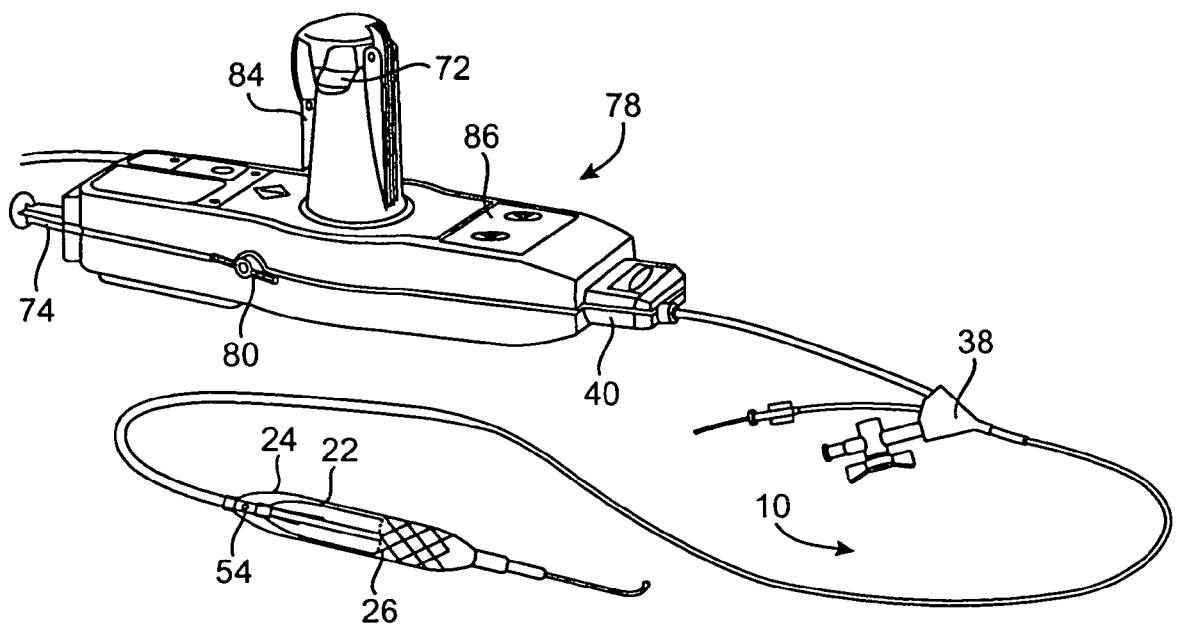

The vacuum space 52 may be provided by a simple fixed vacuum chamber 64 coupled to the vacuum space 52 by a vacuum lumen 66 of the body 12 via a vacuum port 68 (See FIG. 3). In one embodiment, a positive displacement pump (ideally being similar to a syringe) is disposed within handle 74 and may be actuated by actuator 75, as seen in FIG. 6. The vacuum space 52 should comprise a small volume of vacuum in the range from 1 mL to 100 mL, preferably 10 mL or less, as a smaller vacuum space 52 facilitates detection of a change in the amount of vacuum when a small amount of fluid leakage occurs. The battery may be electrically coupled to a heater 61 for heating the fluid supply 62 and cryogenic fluid therein to room temperature or warmer so as to enhance the fluid pressure and cooling system performance, as is more fully described in co-pending application Ser. No. 09/268,205, the full disclosure of which is incorporated herein by reference. The cryogenic fluid supply 62, heater 61, and battery 60 for powering the circuit may be packaged together in an energy pack 70, as seen in FIG. 7. The energy pack 70 is detachable from a proximal handle 74 of the catheter body and disposable. A plurality of separate replaceable energy packs 70 allow for multiple cryogenic cooling cycles. Additionally, an audio alert or buzzer 76 may be located on the handle 74, with the buzzer providing an audio warning unless the handle is maintained sufficiently upright to allow flow from the fluid supply 62. The cryotherapy catheter may additionally comprise a hypsometer 72 coupled to the volume by a thermistor (via thermistor wires 71), thermocouple, or the like located in the first balloon 22 or handle to determine the pressure and/or temperature of fluid in the first balloon 22. The hypsometer allows for accurate real time measurements of variables (pressure, temperature) that effect the efficacy and safety of cryotherapy treatments.

Figure 8A:
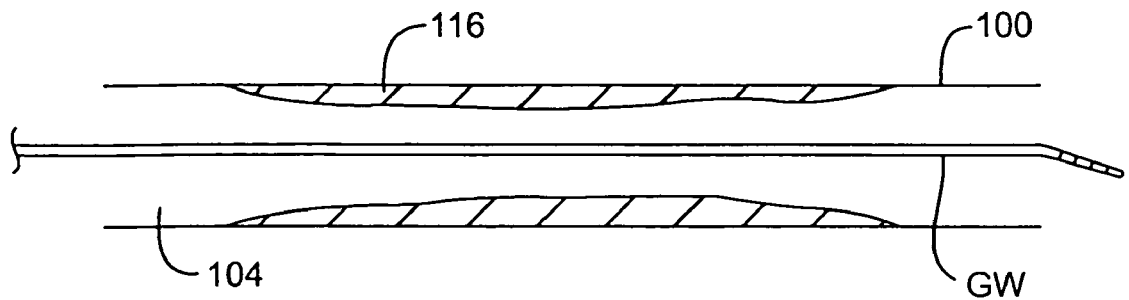
FIGS. 8A-8D illustrate use of the catheter of FIG. 3 for treatment of potential vessel dissections.
Figure 8B:
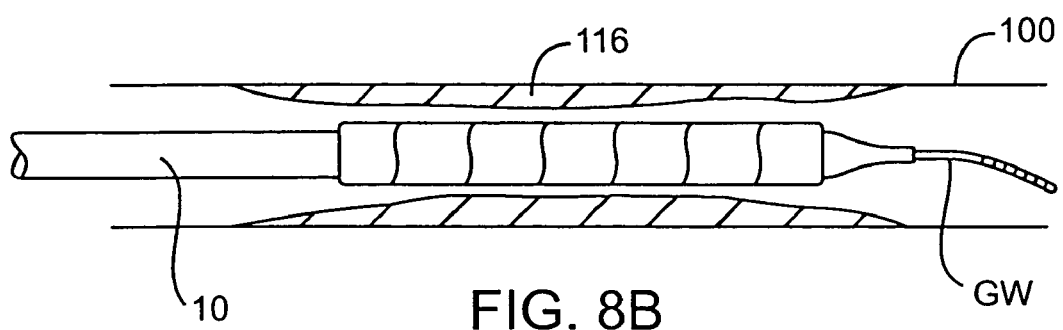
Figure 8C:
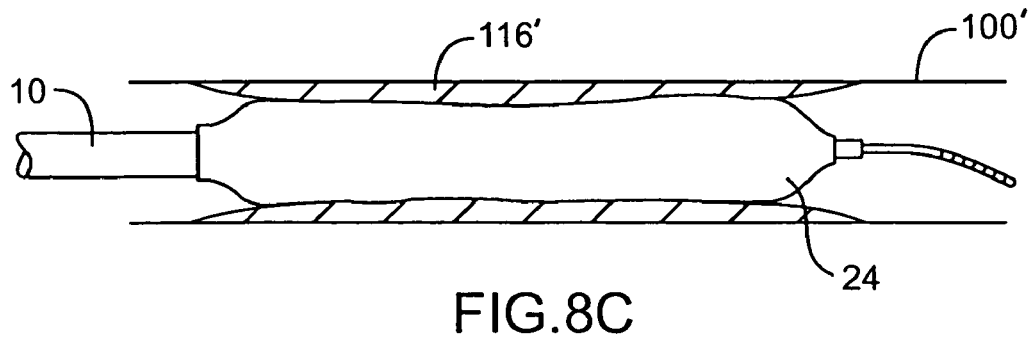

Referring now to FIGS. 8A through 8D, use of the cryotherapy catheter 10 of FIG. 3 for treatment of potential vessel dissections 102 will be described. As illustrated in FIG. 8A and 8B, catheter 10 will be introduced into a lumen 104 of the blood vessel 100 over a guidewire GW. The blood vessel 100 may be any blood vessel in the patient's vasculature, including veins, arteries, and particularly coronary arteries. The blood vessel 100 will typically be at least partially stenosed 116. The first balloon 22 is positioned within the blood vessel lumen 104 adjacent the potential dissection 102. Cryogenic cooling fluid is introduced into the first balloon 22 (in which it often vaporizes) and exhausted. The second balloon 24 expands to radially engage the vessel wall, as illustrated by FIG. 8C. The vaporized fluid serves to inflate balloon 22 (and expand balloon 24) so as to simultaneously dilate and cool the stenosed blood vessel 100. The blood vessel 100 is cooled to a temperature and for a time sufficient to remodel the blood vessel such that dissections 102 of the blood vessel wall 100 are reduced. The cooling treatment will be directed at all or a portion of a circumferential surface the vessel lumen 104.

Figure 8D:
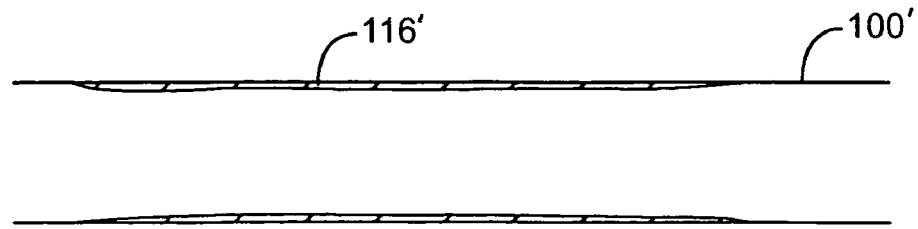

Preferably cooling will reduce and/or inhibit potential dissections so as to produce a "stent-like" angiographic result (i.e. dissection free lumen without the use of a stent), as shown in FIG. 8D. Cooling may alter mechanical properties of the blood vessel 100' or plaque 116' thereon so the that fissuring or tearing of the blood vessel wall or plaque thereon is reduced. Particularly, the blood vessel wall 100' and/or plaque 116' is solidified so that there is not such a great disparity in compliance between the two. As such, the dilatation force applied by the angioplasty cooling balloon is more evenly distributed so that tearing of the vessel at the junction between the vessel wall and plaque is minimized. Cooling may further enhance bonding between layer of the blood vessel wall 100' (i.e., intimal layer, medial layer, adventitial layer) so that fissuring or tearing of the blood vessel wall is reduced. Heat transfer will also be inhibited between the first and second balloons 22, 24 by the thermal barrier 26 so as to limit cooling to a desired temperature profile. Additionally, containment of the first and second balloons 22, 24 will be monitored during cooling by the fluid shutoff mechanism (see FIG. 5).

Suitable cryogenic fluids will preferably be non-toxic and may include liquid nitrous oxide, liquid carbon dioxide, cooled saline and the like. The cryogenic fluid will flow through the supply lumen 18 as a liquid at an elevated pressure and will vaporize at a lower pressure within the first balloon 22. For nitrous oxide, a delivery pressure within the supply lumen 18 will typically be in the range from 600 psi to 1000 psi at a temperature below the associated boiling point. After vaporization, the nitrous oxide gas within the first balloon 22 near its center will have a pressure typically in the range from 50 psi to 150 psi. Preferably, the nitrous oxide gas will have a pressure in the range from 75 psi to 125 psi in a peripheral artery and a range from about 75 psi to 125 psi in a coronary artery.

Generally, the temperature of the outer surface of the first balloon 22 will be in a range from about 0° C. to about −50° C. Preferably, the temperature of the outer surface of the first balloon 22 in a peripheral artery will be in a range from about 0° C. to about −40° C. The temperature of the outer surface of the second balloon 24 will be in a range from about −3° C. to about −15° C. This will provide a desired treatment temperature in a range from about −3° C. to about −15° C. The tissue is typically maintained at the desired temperature for a time period in the range from about 1 to 60 seconds, preferably being from 20 to 40 seconds. Vessel dissection minimization may be further enhanced by repeating cooling in cycles, typically with from about 1 to 3 cycles, with the cycles being repeated at a rate of about one cycle every 60 seconds.

Figure 9A:
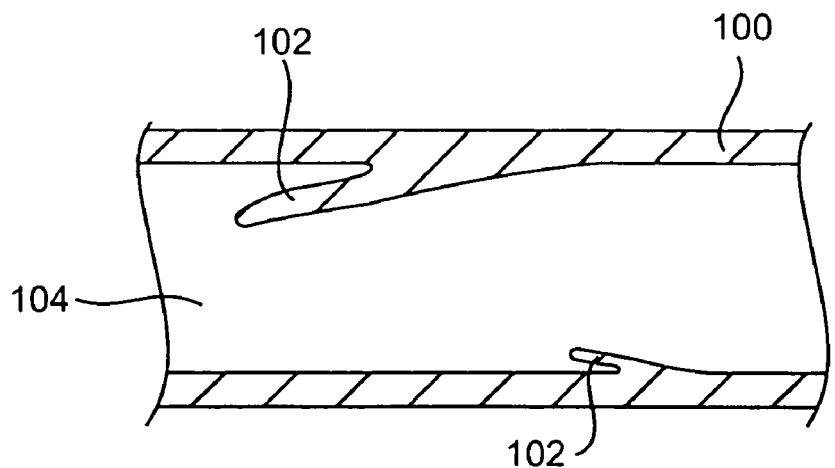
FIGS. 9A-9C illustrate use of the catheter of FIG. 3 for treatment of existing vessel dissections.
Figure 9B:
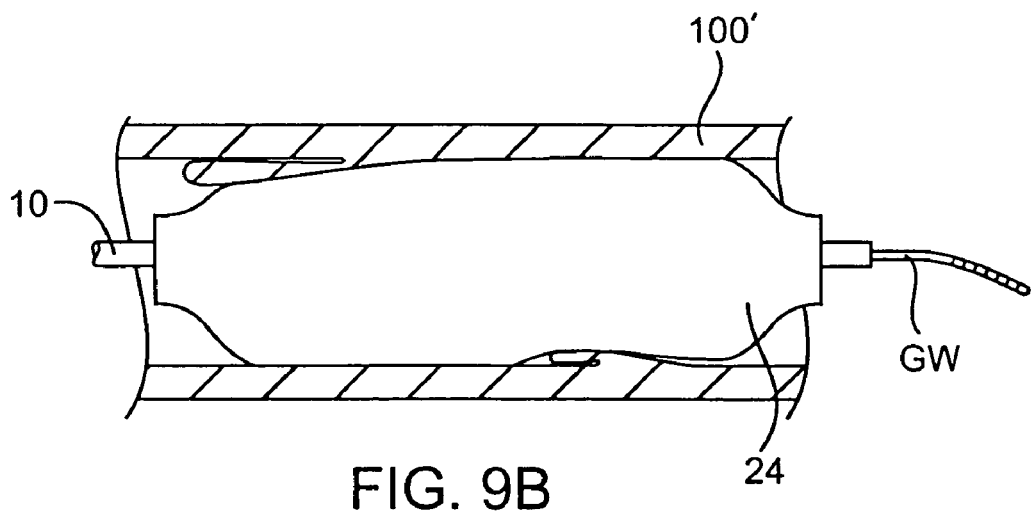
Figure 9C:
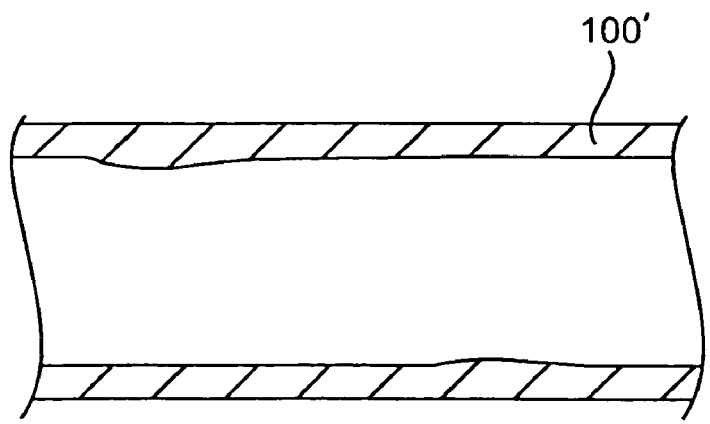

Referring now to FIGS. 9A through 9C, the cooling step may also tack or re-attach existing vessel dissections 102 resulting from a prior angioplasty procedure into the blood vessel wall 100 to produce a "stent-like" angiographic result, as shown in FIG. 9C. Cooling may additionally comprise adhering the cooling balloon 24 to the blood vessel or plaque thereon so as to minimize any slippage of the cooling balloon and in so doing further allow for controlled dilatation of the vessel.

Figure 10A:
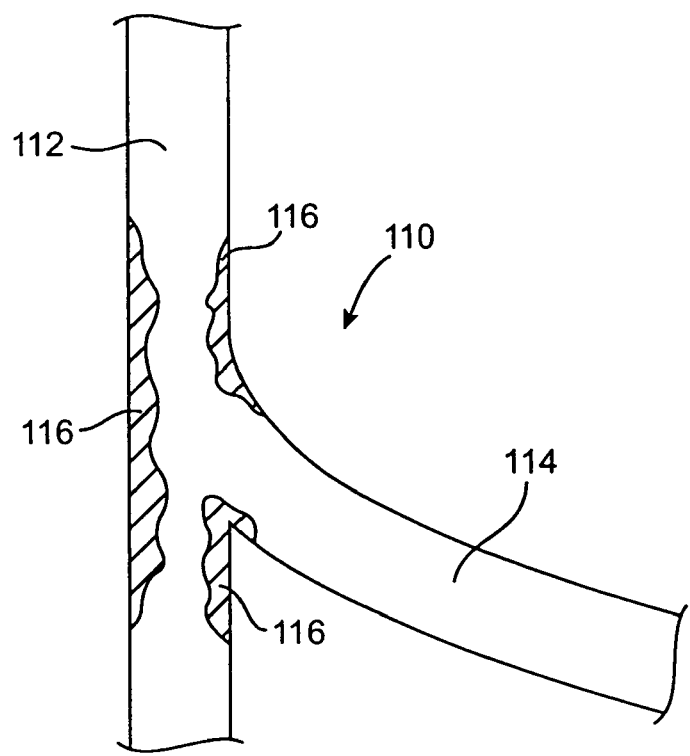
FIGS. 10-10C illustrate use of the catheter of FIG. 3 for treatment of side branch occlusion.
Figure 10B:
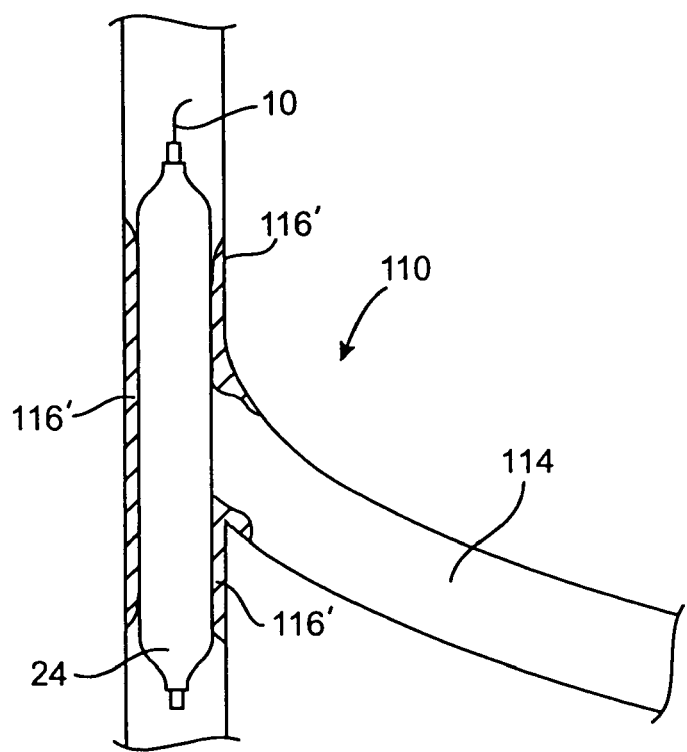
Figure 10C:
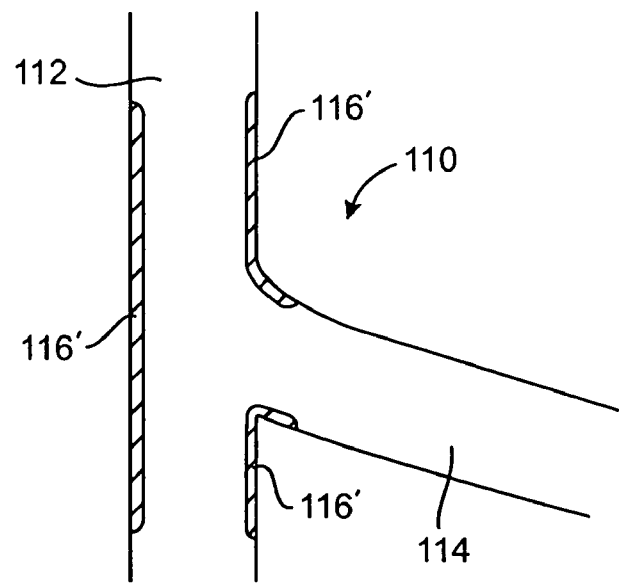

Referring now to FIGS. 10A through 10C, use of the cryotherapy catheter 10 of FIG. 3 for treatment of side branch occlusion in a bifurcated blood vessel 110 will be described. As illustrated in FIG. 10A, the bifurcated blood vessel 110 has a side branch 114 and a main branch 112, the main branch 112 having plaque 116 disposed thereon. In some instances, the side branch 114 may also be at least partially stenosed 116. A catheter 10 is introduced into a lumen of the main branch 112 and a first balloon 22 positioned within the main branch 112 adjacent the plaque 116. Cryogenic cooling fluid is introduced into the balloon 22 and exhausted. A second balloon 24 is expanded to radially engage the main branch lumen, as seen in FIG. 10B, and an inner surface of the main branch 112 is dilated and cooled to a temperature and for a time sufficient to inhibit plaque shift from the main or primary branch 112 into the adjacent or side branch 114. Cooling may alter mechanical properties of the plaque 116' (i.e. plaque compliance) so that plaque shift from the main branch 112 to the side branch 114 is inhibited, as seen in FIG. 10C. In particular, cooling may solidify the plaque 116' so that it is less amorphous and thus less susceptible to shifting. Plaque solidification 116' may further be enhanced by the formation of a temporary ice cap on an orifice of the side branch 114 due to a small portion of the cryoplasty balloon 24 coming into contact with blood cells (not shown).

Figure 11:
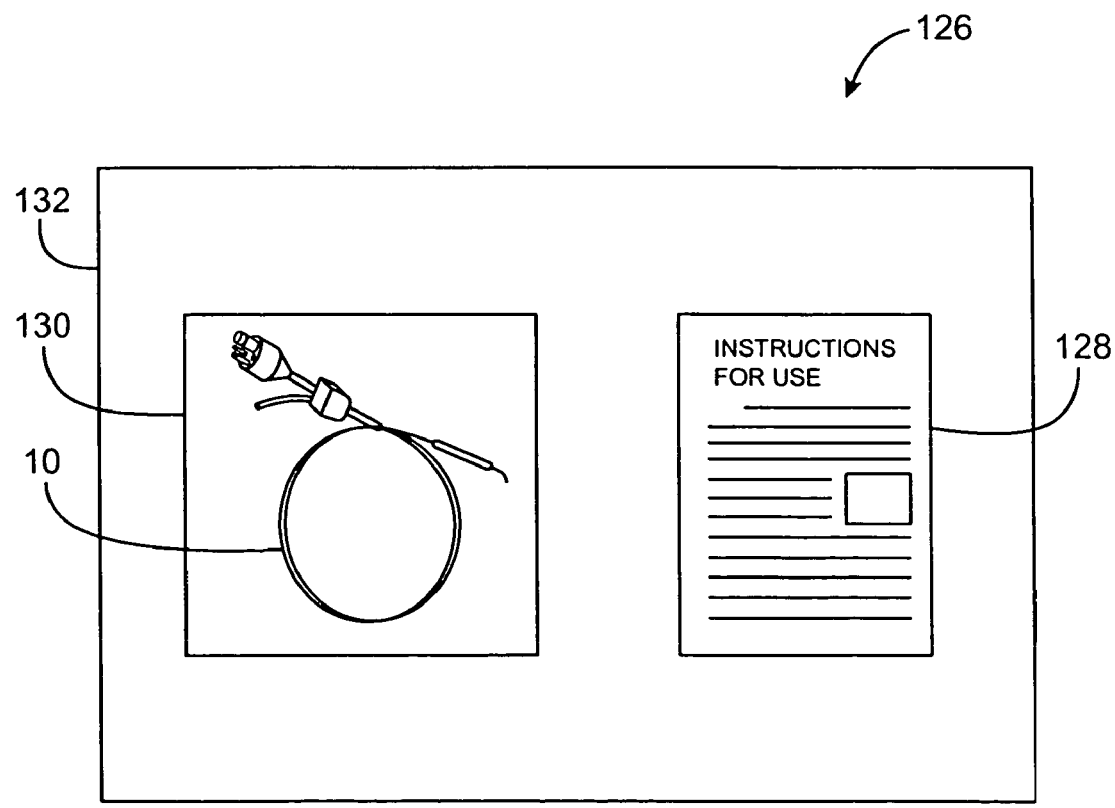
FIG. 11 illustrates a vessel dissection or side branch occlusion treatment kit including the apparatus of FIG. 3 and instructions for use.
Figure 12B:
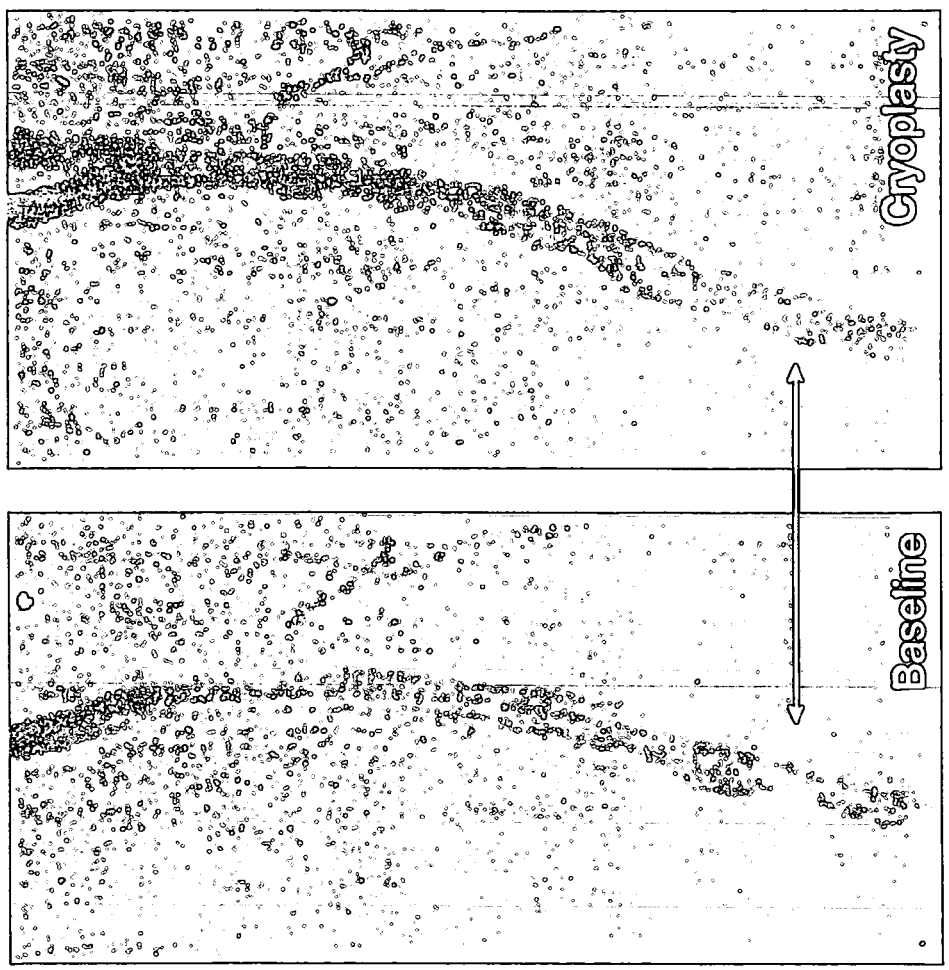
FIGS. 12A through 13E are angiographic results of experiments showing an actual and observed reduction in stenosis with a minimum amount of vessel dissection and side branch occlusion as described in the two Experimental sections provided hereinbelow.
Figure 12A:
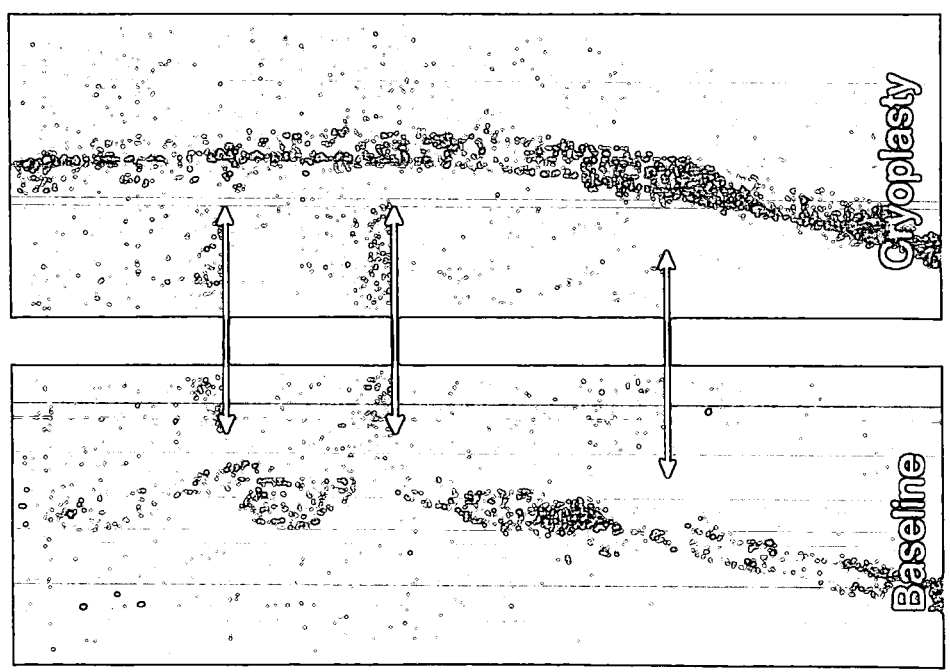
Figure 12C:
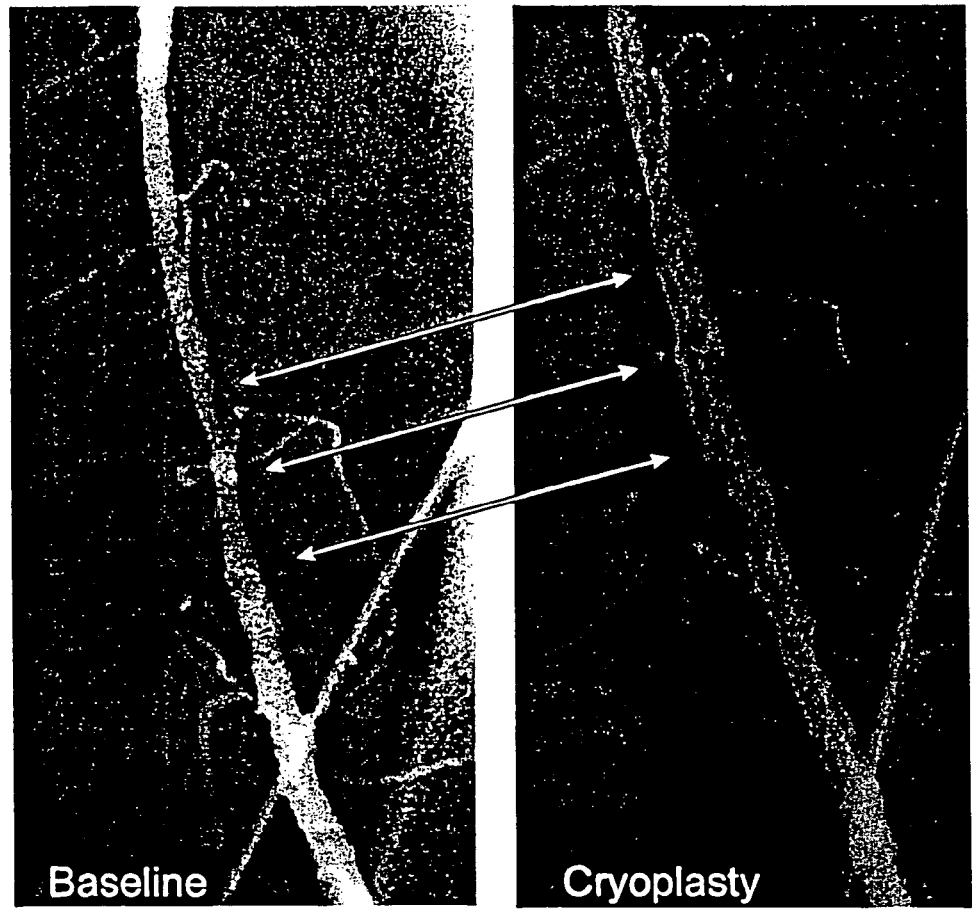
Figure 12D:
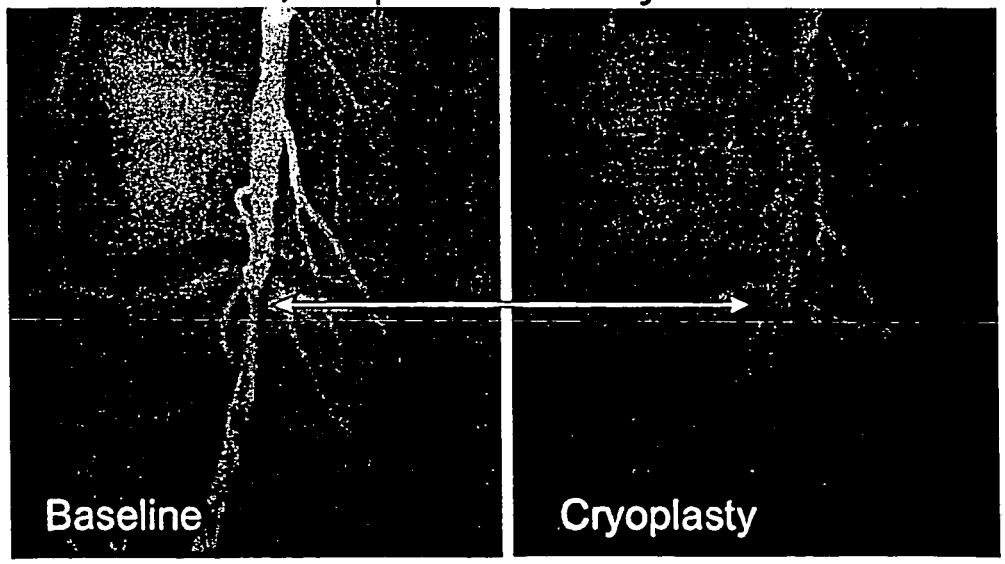
Figure 12E:
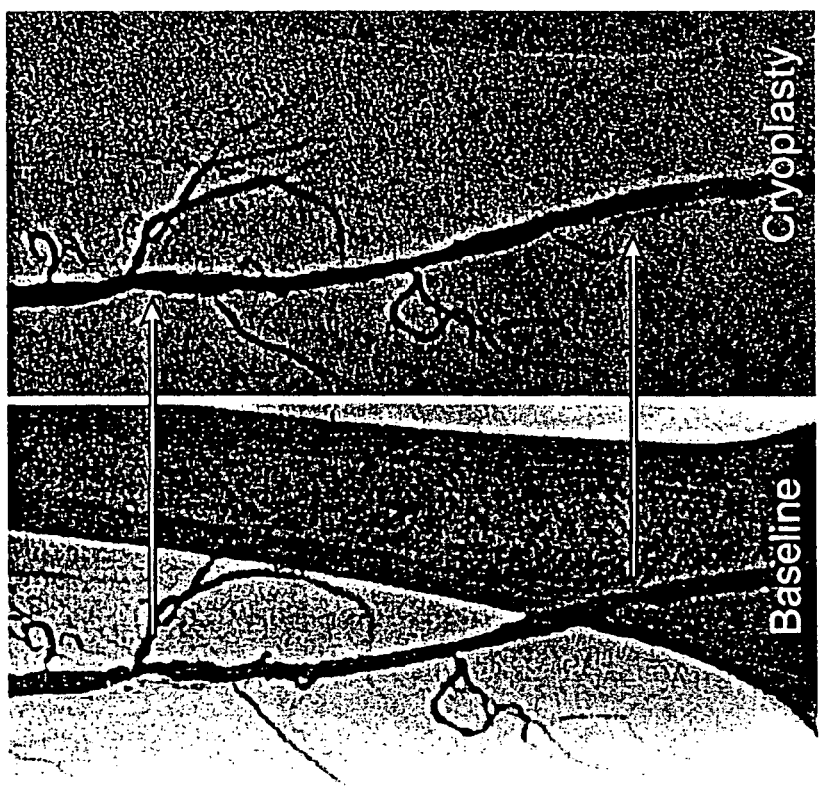
Figure 12F:
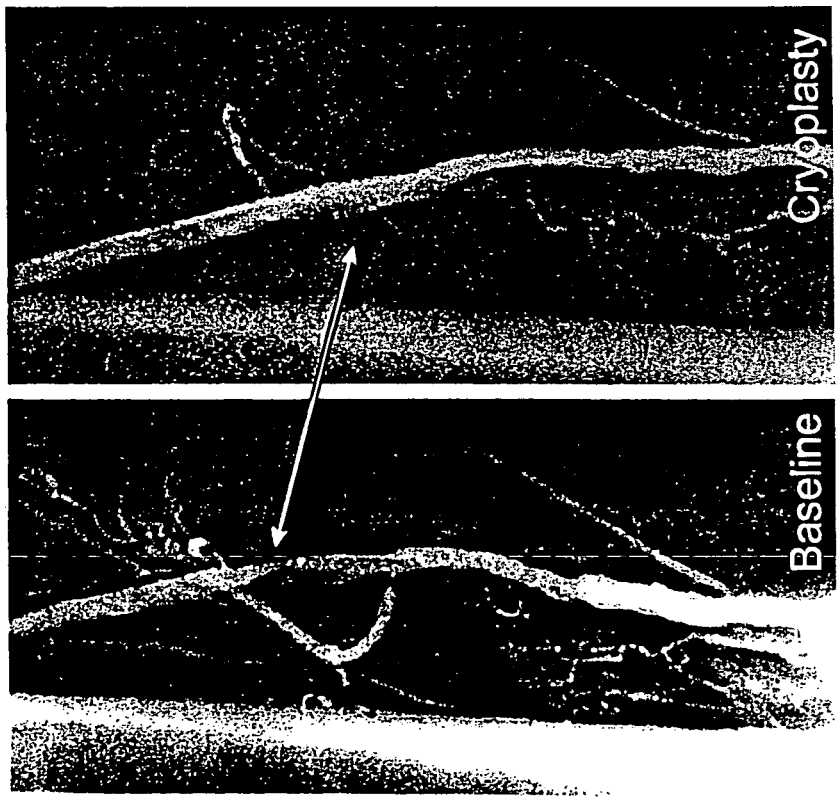
Figure 12H:
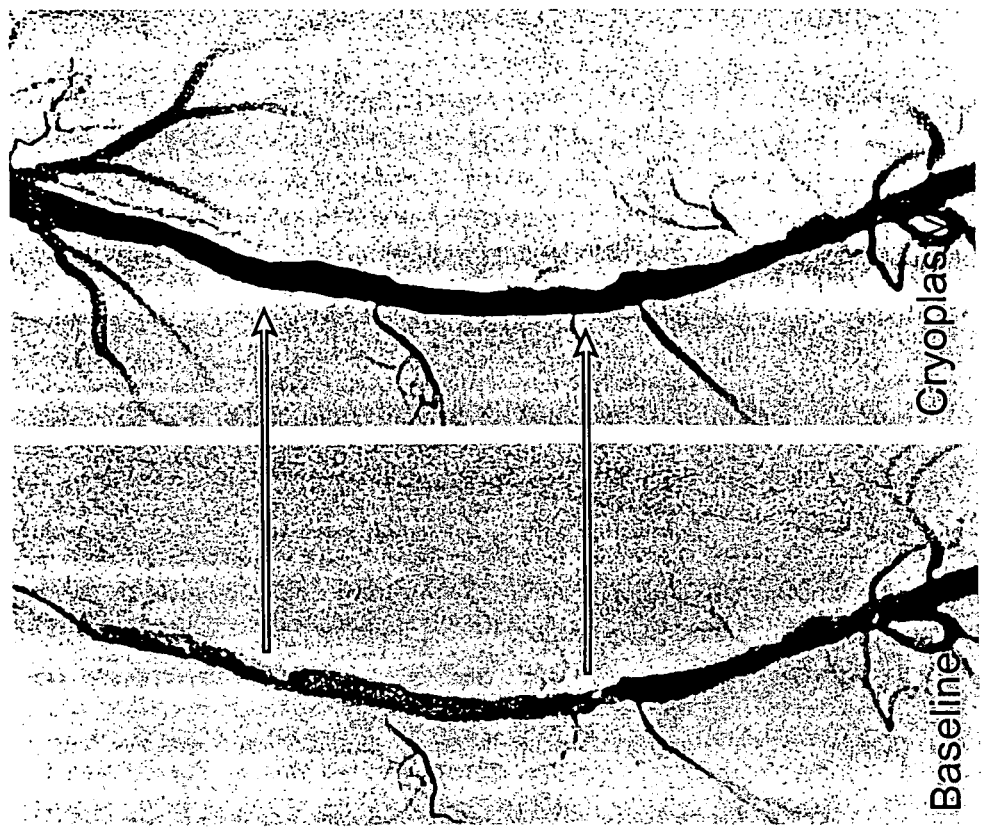
Figure 12G:
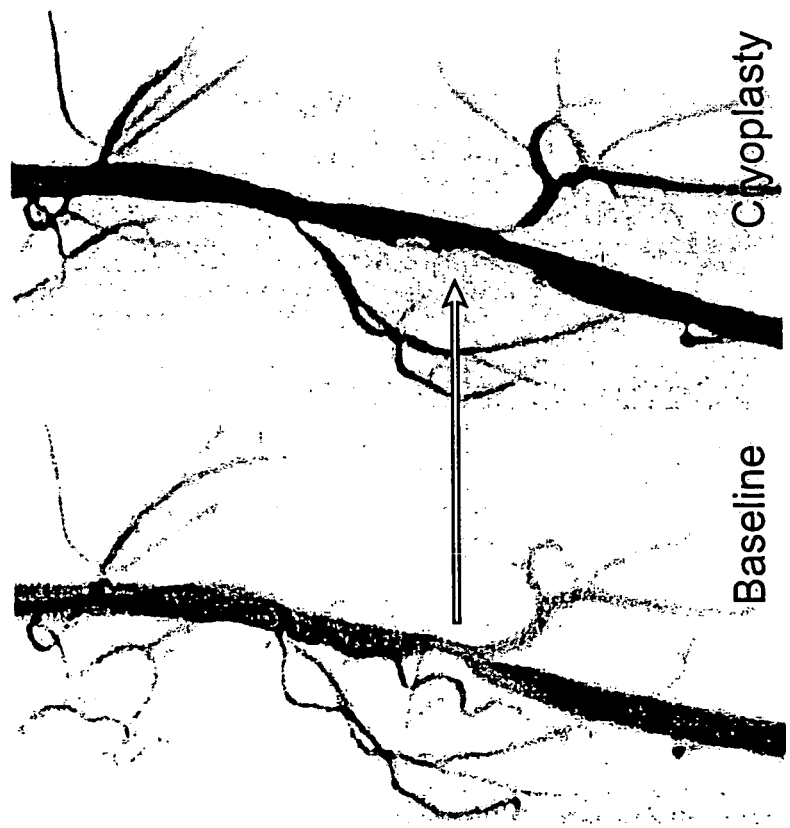
Figure 12J:
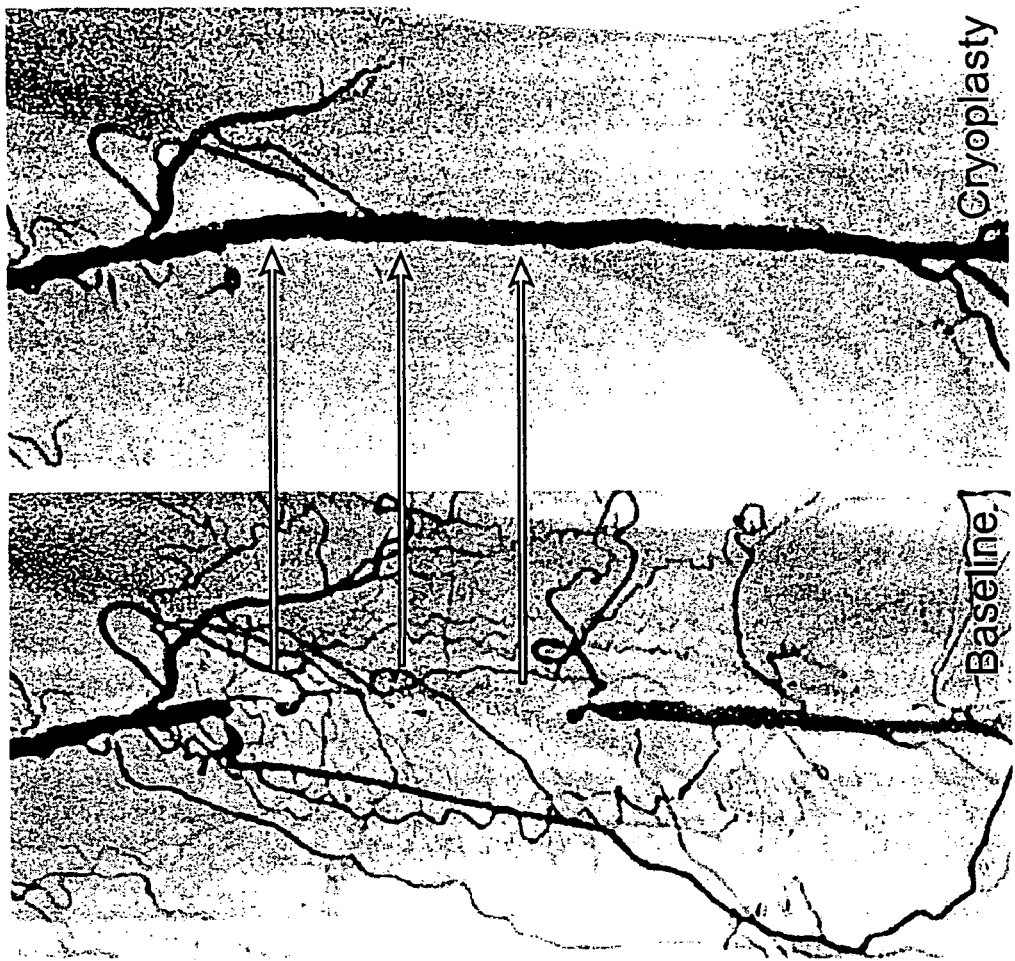
Figure 12I:
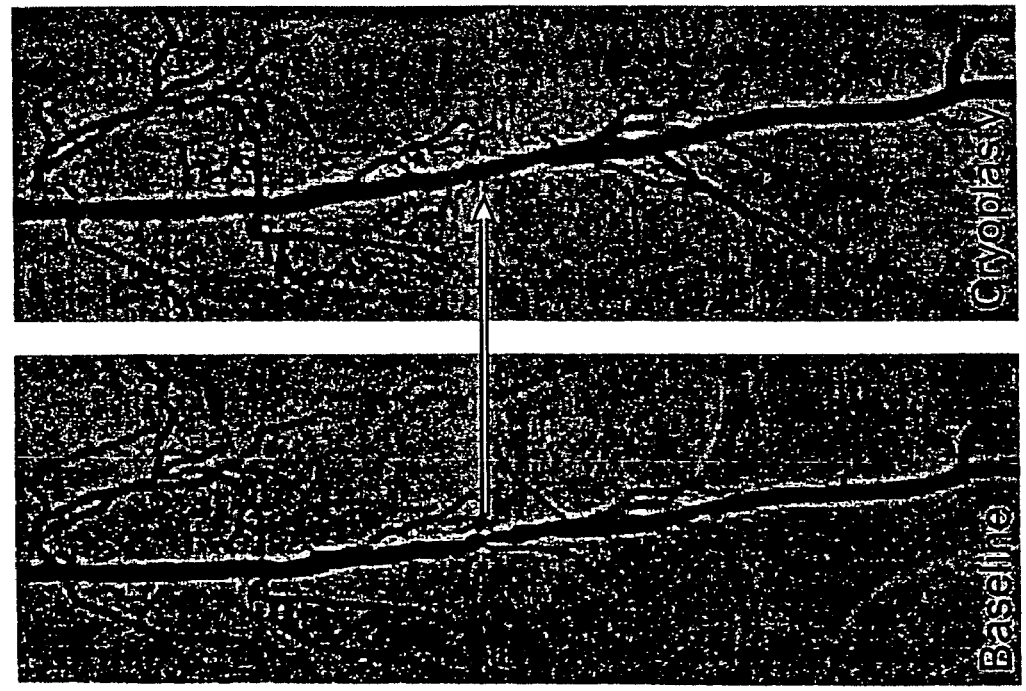
Figure 12L:
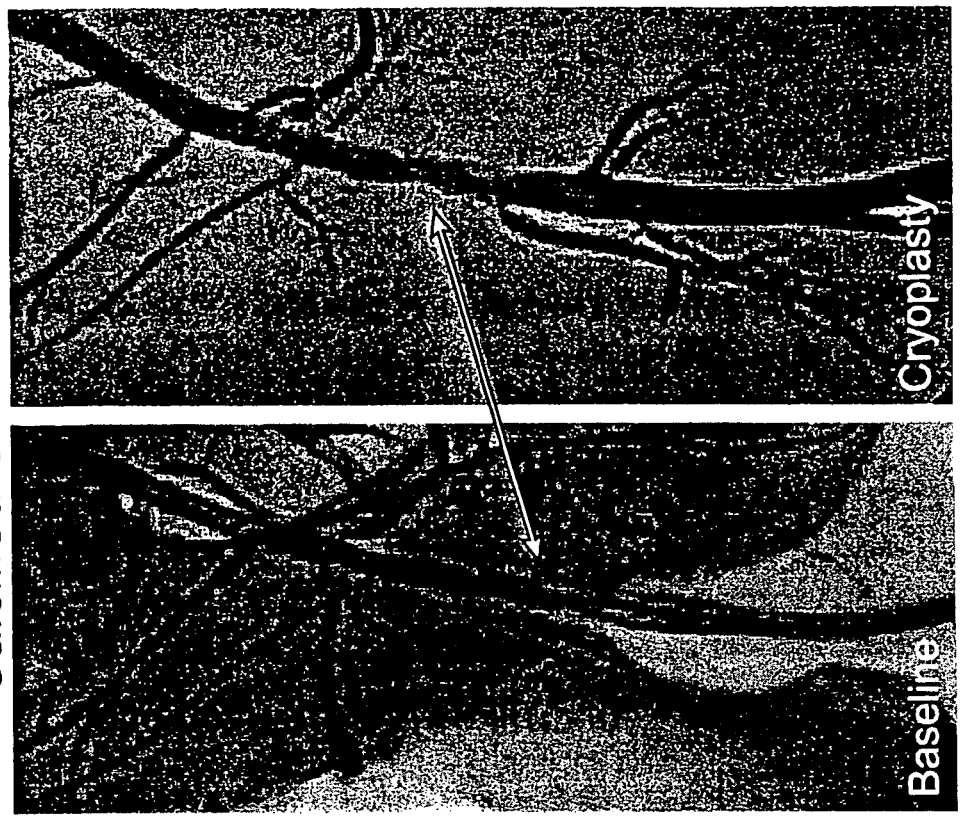
Figure 12K:
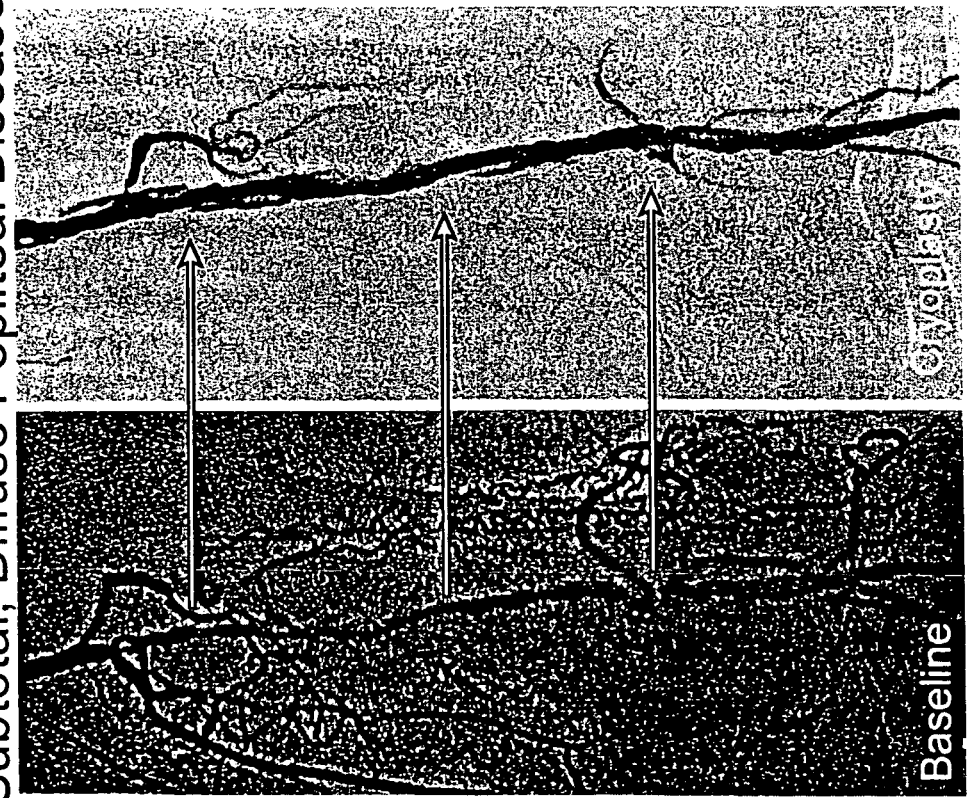
Figure 13D:
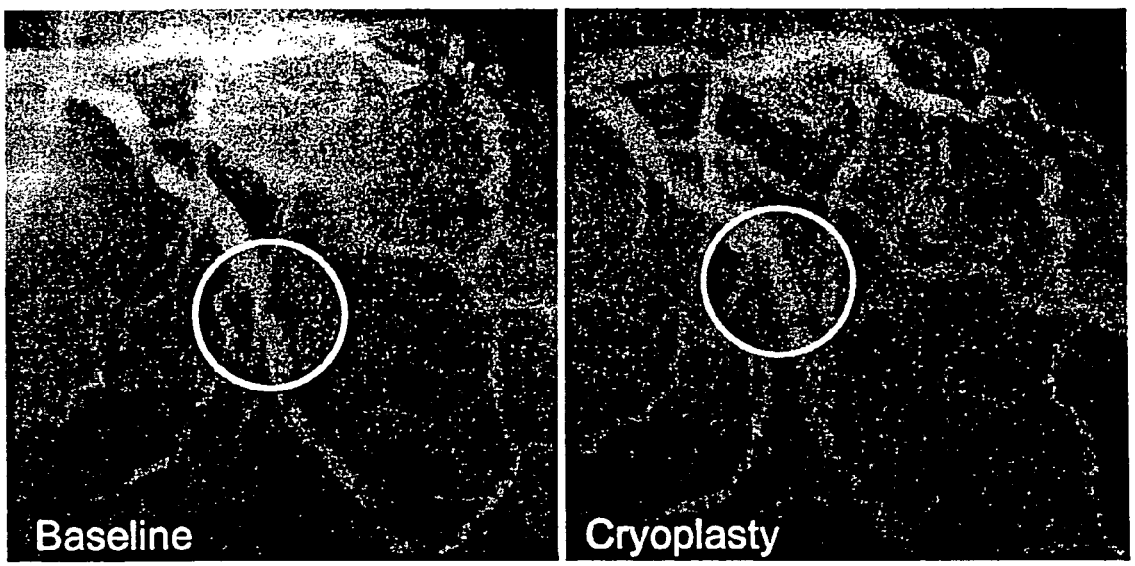
Figure 13E:
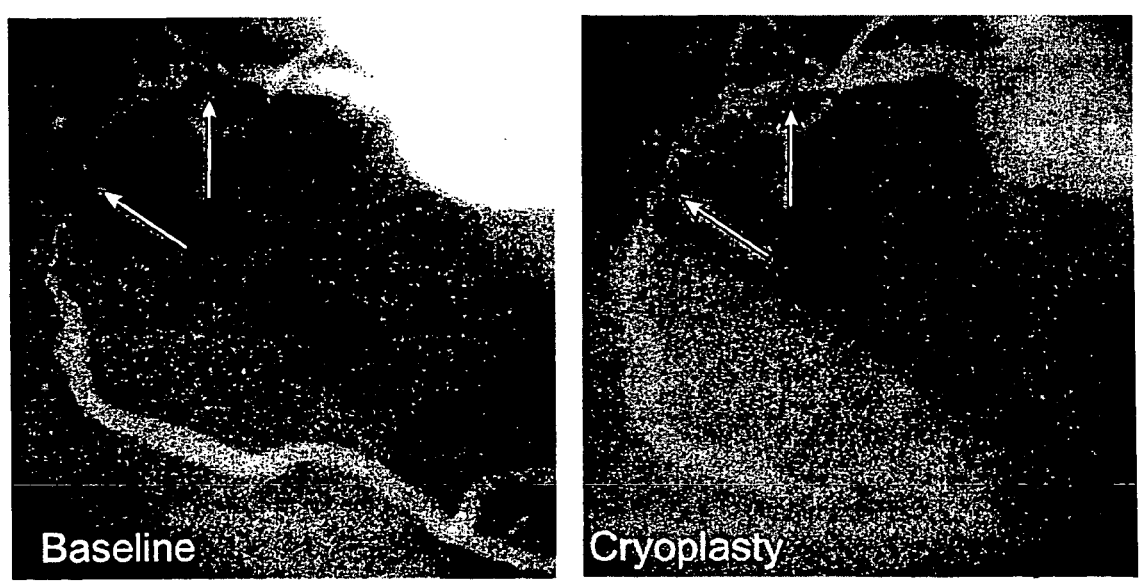

A kit 126 including a catheter 10 and instructions for use 128 is illustrated in FIG. 11. Catheter 10 may comprise the dual balloon catheter of FIG. 3 or a catheter having a proximal end, a distal end, and a cooling member near its distal end. Instructions for use 128 may describe any of the associated method steps set forth above for treatment of vessel dissections and/or side branch occlusion. Instructions for use 128 will often be printed, optionally appearing at least in part on a sterile package 130 for balloon catheter 10. In alternative embodiments, instructions for use 128 may comprise a machine readable code, digital or analog data graphically illustrating or demonstrating the use of balloon catheter 10 to treat vessel dissections and/or side branch occlusion. Still further alternatives are possible, including printing of the instructions for use on packaging 132 of kit 126, and the like. In the following Experimental sections, protocol and results of human clinical studies are given. In particular, angiographic images show a baseline where a significant amount of plaque is present within a lumen of a vessel wall, particularly the superficial femoral artery or popliteal artery. The effects of cryoplasty dilatation are captured by another set of angiographic images which generally show alleviation of the stenotic condition with a minimum amount of vessel dissection and side branch occlusion.

Experimental I:

Peripheral CryoPlasty Clinical Experience

Purpose

Human clinical cases were conducted to evaluate the safety and effectiveness of the CVSi CryoPlasty Catheter and CryoInflation Unit in the dilation of stenotic lesions in diseased superficial femoral and popliteal arteries. Patients with peripheral vascular disease were treated with the CVSi CryoPasty System. This was a non-randomized registry of fourteen (14) patients.

Patient Selection

The interventionalists for these cases identified patients with stenotic lesions in the superficial femoral artery (SFA) and popliteal arteries, which were amenable to percutaneous treatment. Eligibility requirements included the following: the patient was at least 18 years of age; the patient had stenotic lesions within the SFA or popliteal artery which required treatment; the target lesion contained a stenosis between 50% and 100%; the patient had a clinical examination within one month prior to treatment including ABI measurement. Patients were excluded if any of the following applied: the patient had an evolving myocardial infarction, or suffered a myocardial infarction within the past 48 hours; the patient was participating currently in another investigational drug or device trial; or the patient suffered a stroke or transient ischemic neurological attack (TIA) within the past two months.

Equipment

Equipment used for these cases may be found in any interventional catheterization laboratory (including but not limited to fluoroscopy unit with cine film acquisition; sterile accessories such as sheaths and guidewires). The test equipment was the CVSi CryoPlasty System, which is composed of the CryoPlasty Catheter, CryoInflation Unit and accessories (battery, battery receptacle, nitrous oxide cylinder). The operating parameters of the current cases are treatment time of 50 seconds and surface temperature of $-10\pm5°$ C.

Methods

Procedures used were no different than typical interventional percutaneous transluminal angioplasty (PTA) procedures. The investigators had a thorough understanding of the technical principals, clinical applications, and risks associated with PTA. In addition, training on the CVSi CryoPlasty System and its Instructions For Use were given prior to clinical use of the device. After diagnostic angiography of the target vessel confirmed the presence of a lesion suitable for endovascular therapy, the patients received the following treatment. The patient was pre-treated with conventional doses of heparin and aspirin. Baseline angiographic images were recorded as illustrated in FIGS. 12A through 12L. The operators chose whether or not to predilate the lesion with other percutaneous transluminal devices. If they did predilate, an angiographic image of the interim outcome was recorded. Next, the CVSi CryoPlasty Catheter was advanced across the lesion, and inflated with the CryoInflation Unit. After deflation, the catheter was either repositioned for additional cryoinflations, or removed. At the conclusion of the procedure, final cryoplasty angiograms were recorded as illustrated in FIGS. 12A through 12L.

Data Collection

Results of the percutaneous interventions were assessed for acute outcomes and in-hospital adverse events. Baseline and post-cryoplasty dilation angiography were compared in each treated section. In addition, ankle-brachial indexes (ABI) were measured and recorded prior to intervention, 24 hours post-intervention, and at one-month (see Results Table I). ABI is an assessment of flow distal to the treated sections. Technical success was based primarily on the acute angiographic appearance and flow characteristics (24-hour ABI) immediately post-cryoplasty dilation compared to the baseline image and the pre-procedural ABI, respectively.

RESULTS TABLE I

CLINICAL SUMMARY OF PERIPHERAL PATIENTS

| Patient No. | Age/Gender | Site | Lesion Description | Ankle-Brachial Indices | | |
|---|---|---|---|---|---|---|
| | | | | Pre | 24 hr | 1 M |
| 1G | 65 yr M | LSFA (ISR) | 80% stenosis distal to stent, 90% stenosis proximal to stent | 0.70 | 1 | 1 |
| 2G | 88 yr F | LSFA-pop | Total occlusion, 10–12 cm | 0.30 | 0.30 | 0 |
| 3G | 74 yr M | LSFA | 98% stenosis with calcified plaque | 0.65 | 1 | 1 |
| 4G | 75 yr M | LSFA | (4) subtotal focal occlusions, calcified, 8–10 cm total length | 0.70 | 1 | 1 |
| 5G | 61 yr M | R pop | 70% focal stenosis | 0.70 | 1 | 1 |
| 6G | 67 yr F | L pop | Subtotal popliteal occlusion, 12–15 cm long | 0.25 | 0.70 | 1 |
| 1C | 52 yr M | RSFA | 70% stenotis, focal calcified lesion | 0.75 | 1 | 1 |
| 2C | 61 yr F | L pop | 15 mm long, 80% stenotic lesion in proximal popliteal and a 10 mm long, 50% stenotic lesion in the mid popliteal | 0.70 | 1.06 | 1 |
| 3C | 63 yr M | LSFA | 10 mm long, 70% stenotic lesion in the proximal SFA and a 10 mm long, 80% stenotic lesion in the distal SFA | 0.85 | 1.06 | 1 |
| 4C | 41 yr M | Right com. fem. | heavily calcified sub-occlusive focal lesion in the right common femoral artery (15 mm long, 90% stenotic) | 0.60 | 1.0 | 1 |
| 5C | 73 yr F | LSFA-pop | diffuse sub-occlusive (12–16 cm long, 70–80% stenotic) disease in proximal to distal SFA, and 2 focal occlusive lesions in mid popliteal artery | 0.57 | 0.84 | 0.75 |
| 6C | 74 yr F | LSFA | 6–8 cm long total occlusion | 0.57 | 0.85 | 0.80 |
| 7C | 57 yr M | LSFA-pop | calcified focal lesions in SFA (15 mm long, 80% stenotic) and in proximal popliteal artery (10 mm long, 70% stenotic). | 0.58 | 0.89 | 0.97 |
| 8C | 61 yr M | RSFA | two adjacent 95% stenotic focal lesions | 0.60 | 1.08 | 0.90 |

Conclusions and Discussion

Procedural safety was demonstrated by the absence of any incidence of acute serious adverse events or acute percutaneous access site and hemorrhagic adverse events. Investigators were able to use the CryoPlasty device for primary treatment (i.e. were able to cross severe stenosis and dilate the lesion with the CVSi device without predilation) in ten of the fourteen cases (71%). Twelve of the fourteen cases (86%) were technical successes based on acute angiographic appearance and flow characteristics, with <30% residual stenosis by visual assessment of the final angiographic results in the treated segments. Within that 12 patient subset of technical success, the 24-hour post-procedural ABI showed improved blood flow to the lower extremity compared to the pre-procedural measurement. Bail-out stenting was not required in any of the cryotreated segments. Some observations that were noted that contributed to the high technical success rate were: minimum amount of vessel dissection post-CryoPlasty dilation (also known as "vessel annealing") and maintained patency of the side branch and collateral vessels at the treated segments (no/minimal plaque shift), as illustrated in FIGS. 12A through 12L and the ABI data in Results Table I.

The registry demonstrated the safety and effectiveness of the CVSi CryoPlasty System in the dilation of stenotic lesions in diseased vessels, and brought to light some distinct advantages of CryoPlasty over conventional PTA dilation that often requires bail-out stenting due to dissection or poor flow characteristics.

Experimental II:

Coronary CryoPlasty Clinical Experience

Purpose

Five patients with coronary artery disease were treated with the CVSi CryoPlasty System to evaluate the safety and effectiveness of the CVSi System in the treatment of de novo and in-stent restenotic lesions. Patients were assessed for acute outcomes and in-hospital adverse events.

Patient Selection

Patients with either a de novo or in-stent restenosis lesion in a coronary artery that was amenable to percutaneous treatment were identified by experienced intervention-alists. Lesion inclusion criteria was very broad and included very complex lesions, such as, lesion lengths ranging from 10 mm to 25 mm, stenoses from 90% to total occlusions, and calcified, fibrotic, and soft plaque. Other contributing factors were severe access angulations, high cholesterol, diabetes, and smoking.

Methods

After diagnostic angiography of the target vessel confirmed the presence of a lesion suitable for endovascular therapy, each patient received the following treatment. The patient was pretreated with conventional doses of heparin and aspirin. Baseline angiographic images were recorded as illustrated in FIGS. 13A through 13E. The operator could choose whether or not to predilate the lesion with conventional transluminal percutaneous procedures. Next, the CVSi CryoPlasty Catheter was advanced across the lesion, and the balloon inflated one or more times with the CVSi CryoInflation Unit. After the final cryotreatment, the balloon was deflated and the CVSi Catheter was removed. At the conclusion of the procedure, a final angiography was recorded as illustrated in FIGS. 13A through 13E.

Results

The operators were able to use the CryoPlasty device for primary therapy (i.e. were able to cross severe stenosis and dilate the lesion with the CVSi device without predilation) in all the lesions (100%). Additionally, the CryoPlasty device provided good tracking in vessels with >90° turns. A total of six lesions were treated (including one patient who had two lesions in one vessel). All of the lesions treated had <30% residual angiographic stenosis in the dilated artery, as illustrated in FIGS. 13A through 13E and the Results Table II. Patients tolerated the procedure well (i.e. no patient sensation of treatment) and four to six week clinical follow-up reports 0% major adverse cardiac events (MACE).

RESULTS TABLE II

CLINICAL SUMMARY OF CORONARY PATIENTS

| BUC # | Age/Sex | Site | Type | Factors | Baseline Stenosis | Treatments/Comments | Residual Stenosis |
|---|---|---|---|---|---|---|---|
| 1 | 64/F | LCx prox 20 mm × 2.75 mm | D | Total occlusion, severe angulation >100°, some calcification | 100% | (2) CryoPlasty Inflations; distal dissection grade B-not requiring stent placement; No pain | 20% |
| 2 | 55/M | LAD prox 15 mm × 3.0 mm | D | Stress angina, ST changes after 25 meters, 237 chol | 90% | (1) CryoPlasty inflation; Occlusion angina | 10% |
| 3 | 49/F | LAD prox 10 mm × 3.0 mm | D | Unstable angina 7 days before, admitted; acute MI 1996; sig. angulation at bifurcation; allergic to ASA; narrowing back to bifurcation | 95% sub-total | (1) CryoPlasty inflation | 0% |
| 4 | 58/F | RCA mid 25 mm × 3.5 | I | Diabetic, hypertension, dyslipidemia, PTCA/stent 11/00; PTCA cutting balloon 2/01 | 95% | (4) CryoPlasty inflations | 30% |
|  |  | RCA prox 10 mm × 3.5 | D |  | 90% | (2) CryoPlasty inflations > Grade B-C dissection > 3.5 mm × 16 mm stent (post cryo) | 0% |
| 5 | 74/M | LCx mid 12 mm × 3.5 mm | D | Colon tumor, surgery prep; calcification | 95% | (1) CryoPlasty | 0% |

Conclusion

Cryogenic treatment of atherosclerotic stenoses may effectively limit restenosis in both coronary and peripheral arteries, as well as minimize the amount of vessel dissections and plaque shift post-CryoPlasty dilation. Clinical trial data illustrates that CryoPlasty may represent a simple solution to one of the most vexing problems experienced to date in interventional therapy.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A method for treating side branch occlusion in a bifurcated blood vessel, the bifurcated blood vessel having a side branch and a main branch, the main branch having plaque disposed thereon, said method comprising:

cooling an inner surface of the main branch to a temperature and for a time sufficient to inhibit plaque shift from the main branch into the side branch wherein the cooling time is in a range from about 1 second to less than 20 seconds, and wherein the cooling temperature of the inner surface of the main branch is in a range from about −3° C. to about −15° C.

2. A method as in claim 1, wherein the main branch is an artery.

3. A method as in claim 1, wherein the plaque comprises a combination of calcium, fat, and lipids.

4. A method as in claim 1, wherein the side branch is subject to occlusion by plaque shift from the main branch into the side branch as a result of treatment of plaque in the main branch.

5. A method as in claim 4, wherein the treatment of plaque in the main branch comprises balloon angioplasty.

6. A method as in claim 5, wherein the cooling step is performed before, during, and/or after balloon angioplasty.

7. A method as in claim 6, wherein the side branch is at least partially stenosed.

8. A method as in claim 7, wherein the treatment of stenosis in the side branch comprises balloon angioplasty.

9. A method as in claim 8, wherein the main branch and side branch are treated simultaneously or sequentially.

10. A method as in claim 1, wherein the cooling step alters mechanical properties of the plaque so that plaque shift from the main branch to the side branch is inhibited.

11. A method as in claim 10, wherein the cooling step solidifies the plaque so that it is less amorphous.

12. A method as in claim 11, wherein plaque solidification is enhanced by the formation of a temporary ice cap on an orifice of the side branch.

13. A method for treating side branch occlusion in a bifurcated blood vessel, the bifurcated blood vessel having a side branch and a main branch, the main branch having plaque disposed thereon, said method comprising:
    introducing a catheter into a lumen of the main branch;
    positioning a balloon within the main branch lumen adjacent the plaque;
    introducing a cryogenic cooling fluid into the balloon;
    exhausting the cooling fluid;
    expanding the balloon to radially engage the main branch lumen; and
    cooling an inner surface of the main branch to a temperature and for a time sufficient to inhibit plaque shift from the main branch into the side branch
    wherein the cooling time is in a range from about 1 second to less than 20 seconds, and wherein the cooling temperature of the inner surface of the main branch is in a range from about −3° C. to about −15° C.

* * * * *